United States Patent
Thielen et al.

(10) Patent No.: US 9,909,176 B2
(45) Date of Patent: Mar. 6, 2018

(54) EFFICIENT DEEP SEQUENCING AND RAPID GENOMIC SPECIATION OF RNA VIRUSES (VRNASEQ)

(71) Applicant: The Johns Hopkins University, Baltimore, MD (US)

(72) Inventors: Peter M. Thielen, Ellicott City, MD (US); Jared D. Evans, Ellicott City, MD (US); Thomas S. Mehoke, Washington, DC (US); Joshua T. Wolfe, Bethesda, MD (US)

(73) Assignee: The Johns Hopkins University, Baltimore, MD (US)

( * ) Notice: Subject to any disclaimer, the term of this patent is extended or adjusted under 35 U.S.C. 154(b) by 17 days.

(21) Appl. No.: 14/841,981

(22) Filed: Sep. 1, 2015

(65) Prior Publication Data

US 2016/0076094 A1 Mar. 17, 2016

Related U.S. Application Data

(60) Provisional application No. 62/047,172, filed on Sep. 8, 2014.

(51) Int. Cl.
*C12Q 1/68* (2006.01)
*C12Q 1/70* (2006.01)

(52) U.S. Cl.
CPC ............ *C12Q 1/6874* (2013.01); *C12Q 1/70* (2013.01)

(58) Field of Classification Search
None
See application file for complete search history.

(56) References Cited

PUBLICATIONS

Hoper, et al. (2011) "A Comprehensive Deep Sequencing Strategy for Full-Length Genomes of Influenza A", 6(4):e19075 (8 pages).*
https://tools.thermofisher.com/content/sfs/manuals/18267.pdf, Author Unknown, Published by Invitrogen, Carlsbad, CA., "cDNA Synthesis System, Cat. No. 18267-013", Feb. 1, 2001, 36 pages, printed.*
https://ehr.primate.wisc.edu/wiki/WNPRC/WNPRC_Units/Research_Services/Genetics_Services/Public/download.view?entityId=469a47b9-8451-102c-8dc0-493dbd27fbc9&name=2014April29_Illumina_WhitePaper.pdf, Gellerup, et al. (Apr. 2014) "Viral RNA Genome Characterization via Illumine MiSeq Technology", UW—Madison, 5 pages printed.*
Racaniello (2013) "How man viruses on Earth?" published online: http://www.virology.ws/2013/09/06/how-many-viruses-on-earth/, no location available, (Dr. Racaniello is a renown virologist at Columbia University, NY, NY), 6 pages printed.*

* cited by examiner

*Primary Examiner* — Robert M Kelly
(74) *Attorney, Agent, or Firm* — Todd R. Farnsworth

(57) ABSTRACT

A method for limited input whole genome sequencing of RNA viruses includes isolating a viral RNA sample, converting the viral RNA sample to a double-stranded viral cDNA sample, constructing a double-stranded viral cDNA amplicon library from the double-stranded viral cDNA sample, and sequencing the double-stranded viral cDNA amplicon library to obtain a double-stranded viral cDNA sample sequencing read.

20 Claims, 26 Drawing Sheets

SEQUENCE LISTING

<160> NUMBER OF SEQ ID NOS: 15

<210> SEQ ID NO 1
<211> LENGTH: 22
<212> TYPE: DNA
<213> ORGANISM: Murine Norovirus

<400> SEQUENCE: 1
agccgatcac aggctccttg gc                                       22

<210> SEQ ID NO 2
<211> LENGTH: 23
<212> TYPE: DNA
<213> ORGANISM: Murine Norovirus

<400> SEQUENCE: 2
ccatcggcca taagagggct ggc                                      23

<210> SEQ ID NO 3
<211> LENGTH: 22
<212> TYPE: DNA
<213> ORGANISM: Murine Norovirus -continued

```
<400> SEQUENCE: 3
acgcacttcc tcaactcagc cg                                              22

<210> SEQ ID NO 4
<211> LENGTH: 20
<212> TYPE: DNA
<213> ORGANISM: Murine Norovirus

<400> SEQUENCE: 4
ggccatgctg atcctggcca                                                 20

<210> SEQ ID NO 5
<211> LENGTH: 21
<212> TYPE: DNA
<213> ORGANISM: Murine Norovirus

<400> SEQUENCE: 5
ccaccaggat gccatccgag a                                               21

<210> SEQ ID NO 6
<211> LENGTH: 23
<212> TYPE: DNA
<213> ORGANISM: Murine Norovirus

<400> SEQUENCE: 6
gtcgacatca gcgcgtggta tga                                             23

<210> SEQ ID NO 7
<211> LENGTH: 21
<212> TYPE: DNA
<213> ORGANISM: Murine Norovirus

<400> SEQUENCE: 7
caacagggtg ggcaccacgt c                                               21

<210> SEQ ID NO 8
<211> LENGTH: 28
<212> TYPE: DNA
<213> ORGANISM: Murine Norovirus

<400> SEQUENCE: 8
caacaacagg gctctcagca taaaccag                                        28

<210> SEQ ID NO 9
<211> LENGTH: 20
<212> TYPE: DNA
<213> ORGANISM: Dengue virus

<400> SEQUENCE: 9
ccttccacra artctctrtt                                                 20

<210> SEQ ID NO 10
<211> LENGTH: 20
<212> TYPE: DNA
<213> ORGANISM: Dengue virus

<400> SEQUENCE: 10
atttccatsc crtaccarca                                                 20

<210> SEQ ID NO 11
<211> LENGTH: 20
<212> TYPE: DNA
```

```
<213> ORGANISM: Dengue virus

<400> SEQUENCE: 11
acrtgccaca ttgtrtgraa                                               20

<210> SEQ ID NO 12
<211> LENGTH: 20
<212> TYPE: DNA
<213> ORGANISM: Dengue virus

<400> SEQUENCE: 12
gaccakccwc ctctbccrca                                               20

<210> SEQ ID NO 13
<211> LENGTH: 20
<212> TYPE: DNA
<213> ORGANISM: Dengue virus

<400> SEQUENCE: 13
gctccmarcc acatgtacca                                               20

<210> SEQ ID NO 14
<211> LENGTH: 54
<212> TYPE: DNA
<213> ORGANISM: Dengue virus

<400> SEQUENCE: 14
gtctcgtggg ctcggagatg tgtataagag acaggggagg ggtctcctct aacc         54

<210> SEQ ID NO 15
<211> LENGTH: 47
<212> TYPE: DNA
<213> ORGANISM: Influenza A virus

<400> SEQUENCE: 15
gtctcgtggg ctcggagatg tgtataagag acagagtaga aacaagg                 47
```

EFFICIENT DEEP SEQUENCING AND RAPID GENOMIC SPECIATION OF RNA VIRUSES (VRNASEQ)

CROSS-REFERENCE TO RELATED APPLICATIONS

This application claims the benefit of U.S. Provisional Application No. 62/047,172 filed on Sep. 8, 2014, the entire contents of which are hereby incorporated herein by reference.

STATEMENT REGARDING FEDERALLY SPONSORED RESEARCH OR DEVELOPMENT

This invention was made with U.S. Government support under 12372-5043735 awarded by the Defense Advanced Research Projects Agency (DARPA). The U.S. Government has certain rights in the invention.

TECHNICAL FIELD

Example embodiments relate generally to methods for limited input whole genome sequencing of RNA viruses.

BACKGROUND

Sequencing of RNA viruses provides crucial insight into viral infection and evolution. However, whole genome sequencing of viruses can be particularly challenging for second-generation platforms due to genome size, structure, and the presence of large amounts of host nucleic acids. Most protocols rely on either gene specific or global RNA amplification to produce sufficient template quantities for ligation-based sequencing library preparation, a process that can potentially introduce errors interpreted as viral quasispecies or major variants. Conversely, total RNAseq, while agnostic to input, requires co-sequencing of host RNA at the cost of depth of coverage over the virus of interest.

Amplification-free sequencing of RNA genomes poses a significant challenge for many library preparation methods, as material must first be converted into double-stranded DNA among an overwhelming pool of host DNA and RNA. The lowest input methods (e.g., Illumina® Nextera XT) require one nanogram of input, or roughly $4.63 \times 10^7$ genome copies of a 10,000 nucleotide viral genome, assuming conversion into double-stranded cDNA is 100% efficient. Sequencing viral samples from the recent Ebola outbreak was the first published account of Nextera-based library preparation for sequencing of an RNA virus without genomic amplification, relying on depletion of host DNA and ribosomal RNA prior to random hexamer-primed cDNA synthesis. Other viral sequencing protocols utilizing transposon-mediated library preparation without genomic amplification have required a minimum of $1 \times 10^{10}$ viral copies per mL of sample, which is unrealistic for most laboratory or clinical sample collection methods. The inefficiencies encountered in these and other protocols are most likely due to the use of inherently loss-prone nucleic acid isolation methods, such as silica columns and gel purifications, as well as the need to co-sequence non-viral host material.

Therefore there remains a need in the art for a method for limited input whole genome sequencing of RNA viruses without genomic amplification, without co-sequencing of non-viral host material, and using improved nucleic acid isolation methods, thereby eliminating potential sources of amplification-induced error and obviating the need for host ribosomal RNA depletion.

BRIEF SUMMARY

One or more embodiments of the invention may address one or more of the aforementioned problems. Certain embodiments according to the present invention provide a method for limited input whole genome sequencing of RNA viruses having a wide variety of applications. In accordance with certain embodiments, the method may comprise isolating a viral RNA sample, converting the viral RNA sample to a double-stranded viral cDNA sample, constructing a double-stranded viral cDNA amplicon library from the double-stranded viral cDNA sample, and sequencing the double-stranded viral cDNA amplicon library to obtain a double-stranded viral cDNA sample sequencing read.

BRIEF DESCRIPTION OF THE DRAWING(S)

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

FIG. 11, as represented by FIGS. 11A-11D, illustrates characterization of a modified universal Influenza A primer for direct primed sequencing according to an example embodiment.

FIG. 12, as represented by FIGS. 12A-12D, illustrates validation of double-stranded murine norovirus (MNV-1) cDNA for use with amplicon library preparation according to an example embodiment.

FIG. 13, as represented by FIGS. 13A-13E, illustrates serotype agnostic direct primed sequencing of dengue virus according to an example embodiment.

Figure 14:
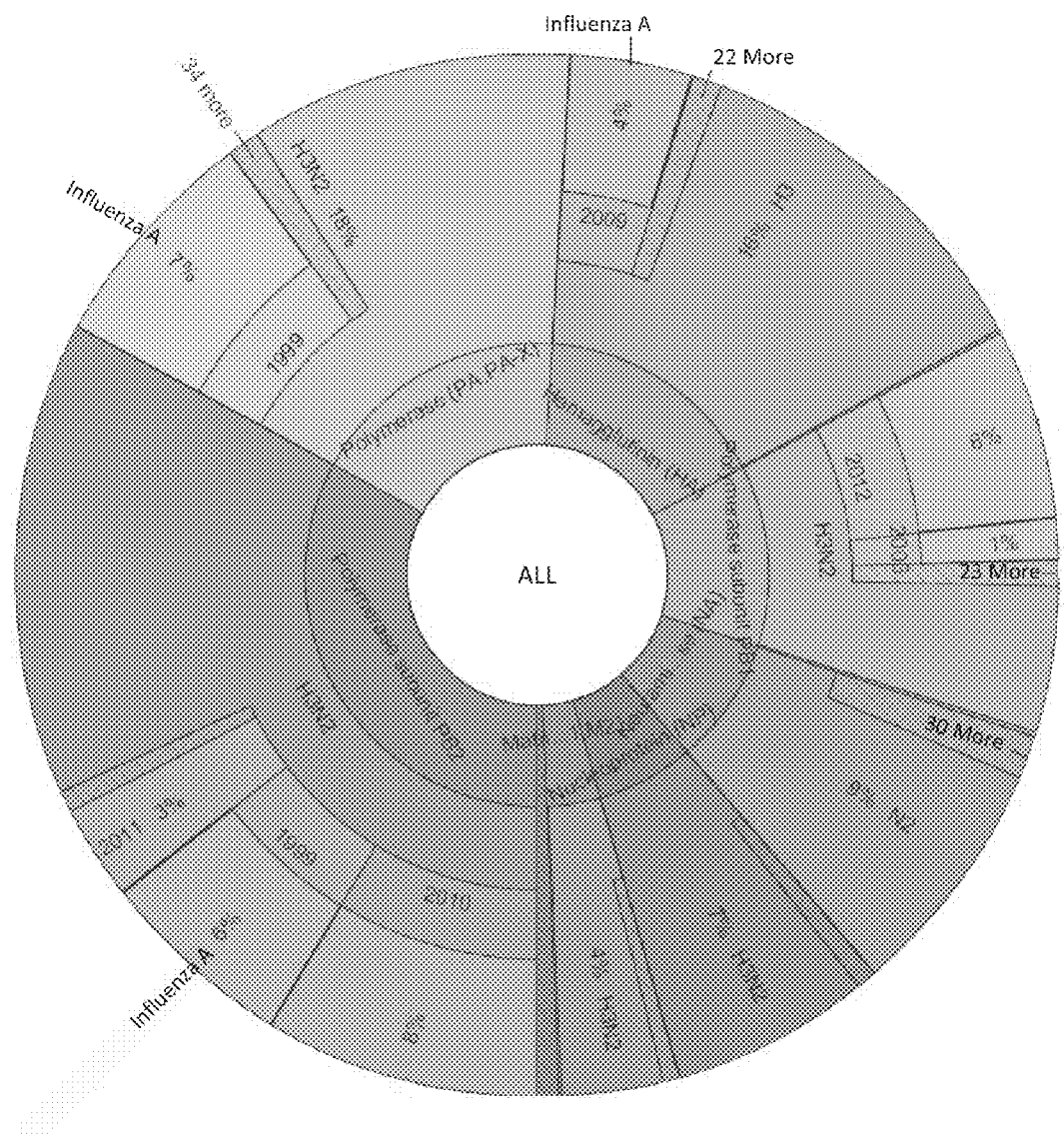

FIG. 14 illustrates a database for an Influenza A-specific implementation of the ultrafast read classifier according to an example embodiment.

Figure 15:
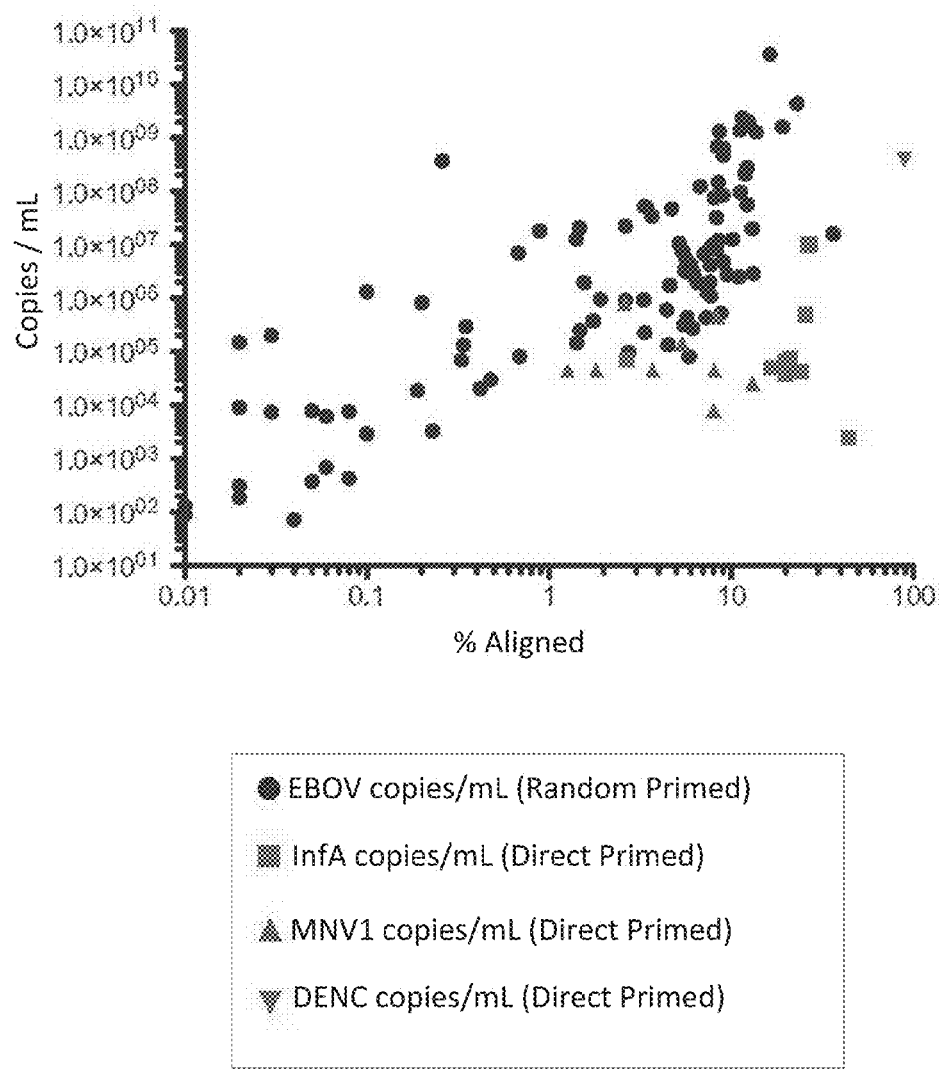

FIG. 15 illustrates improved sequencing efficiency for direct primed sequencing as compared to random primed sequencing according to an example embodiment.

Figure 16:
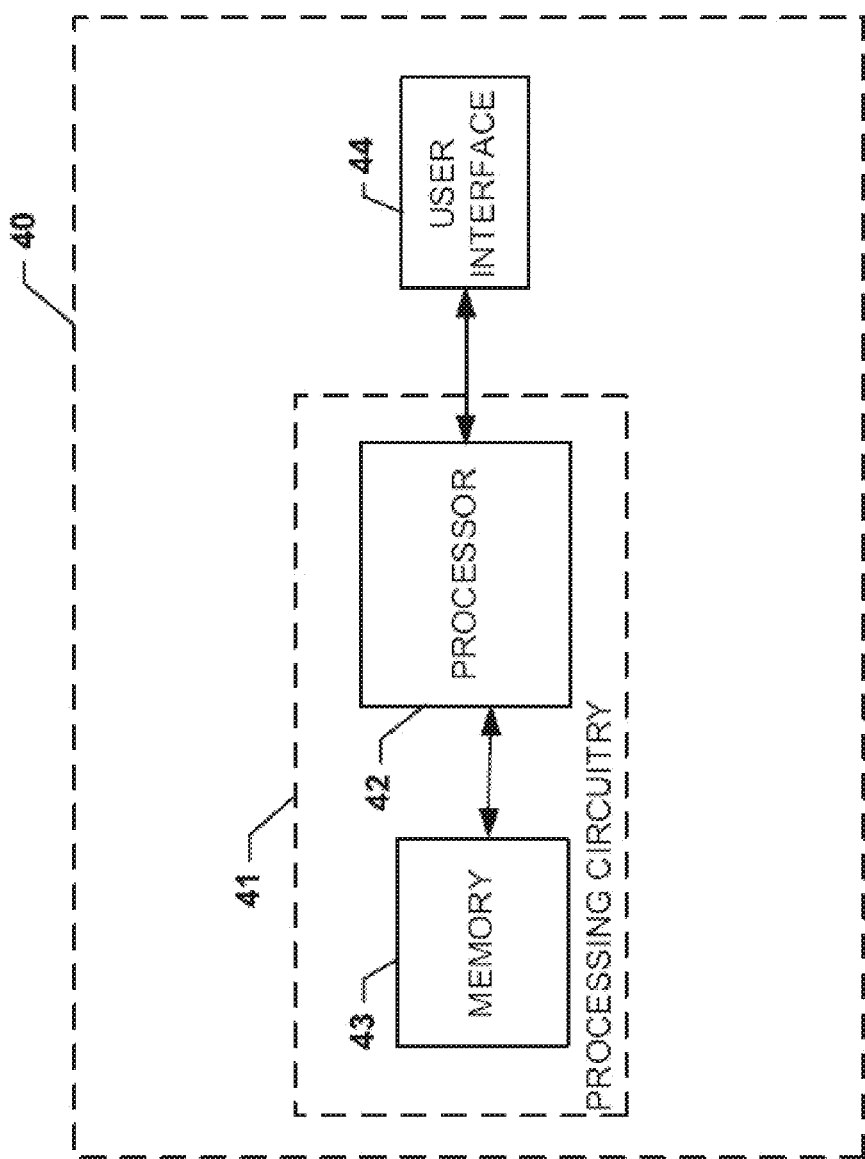

FIG. 16 illustrates a block diagram of an ultrafast read classifier according to an example embodiment.

DETAILED DESCRIPTION

Some example embodiments now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

An example embodiment includes a method for limited input whole genome sequencing of RNA viruses. In accordance with certain embodiments, the method may comprise isolating a viral RNA sample, converting the viral RNA sample to a double-stranded viral cDNA sample, constructing a double-stranded viral cDNA amplicon library from the double-stranded viral cDNA sample, and sequencing the double-stranded viral cDNA amplicon library to obtain a double-stranded viral cDNA sample sequencing read.

The term "tagmentation", as used herein, may comprise reactions that combine fragmentation and ligation reactions into a single step. Sequencing libraries are ordinarily prepared by random fragmentation of a DNA or cDNA sample, followed by 5' and 3' adapter ligation. However, tagmentation reactions combine these reactions into a single step in order to increase the efficiency of the library preparation process. According to certain embodiments, tagmentation reactions may involve providing a double-stranded target nucleic acid and a transposome having a transposase with two transposon end sequences: a "transferred strand" and a "non-transferred strand." The transposome breaks the target nucleic acid into fragments while covalently transferring the transferred strand to a first strand of the fragment; the non-transferred strand of the transposome remains hybridized to the transferred strand.

The term "multiplexed", as used herein, may comprise large numbers of sequencing libraries that have been pooled and sequenced simultaneously during a single sequencing run. To obtain multiplexed libraries according to certain embodiments, unique index sequences may be added to each DNA or cDNA fragment during library preparation so that each sequencing read may be identified and sorted prior to final data analysis. In particular, in some embodiments, for example, two distinct libraries may be attached to unique index sequences during library preparation. Next, libraries may be pooled together and loaded into the same flow cell lane. Libraries may be sequenced together during a single instrument run, and the sequences may be exported to a single output file. A demultiplexing algorithm may then sort the sequencing reads into different files according to the indexes. Finally, each set of sequencing reads may be aligned to the appropriate reference sequence.

The term "ultrafast read classifier", as used herein, may comprise a program for assigning taxonomic labels to metagenomic DNA sequences that, in its fastest mode, classifies 100 base pair reads at a rate of over 4.1 million reads per minute. The ultrafast read classifier contemplated herein is an open source software tool referred to as Kraken. In this regard, the terms "ultrafast read classifier" and "Kraken" may be used interchangeably. Using exact alignment of k-mers rather than inexact alignment of sequences, Kraken achieves classification accuracy comparable to the fastest BLAST program. Kraken's accuracy is made possible by the very large and still-growing number of sequenced microbial genomes, currently numbering over 8,500, which makes it likely that very similar sequences from a given species have previously been seen. Through the use of a novel algorithm to process the disparate results returned by its database, Kraken is able to achieve genus-level sensitivity and precision that are very similar to that obtained by the fastest BLAST program, Megablast.

In some example embodiments, a method for limited input whole genome sequencing of RNA viruses having a wide variety of applications is provided. For example, resulting data may be used for many bioinformatic purposes, including reference alignment, reference-based assembly, variable penetrance single nucleotide variant (SNV) detection, defining minor variants within viral populations, and speciation by the ultrafast read classifier Kraken. In general, methods for limited input whole genome sequencing of RNA viruses according to certain example embodiments may include isolating a viral RNA sample, converting the viral RNA sample to a double-stranded viral cDNA sample, constructing a double-stranded viral cDNA amplicon library from the double-stranded viral cDNA sample, and sequencing the double-stranded viral cDNA amplicon library to obtain a double-stranded viral cDNA sample sequencing read. In addition, according to certain embodiments, this process may be easily automatable for high-throughput analysis of large numbers of samples or to avoid exposure to particular pathogens.

Figure 1:
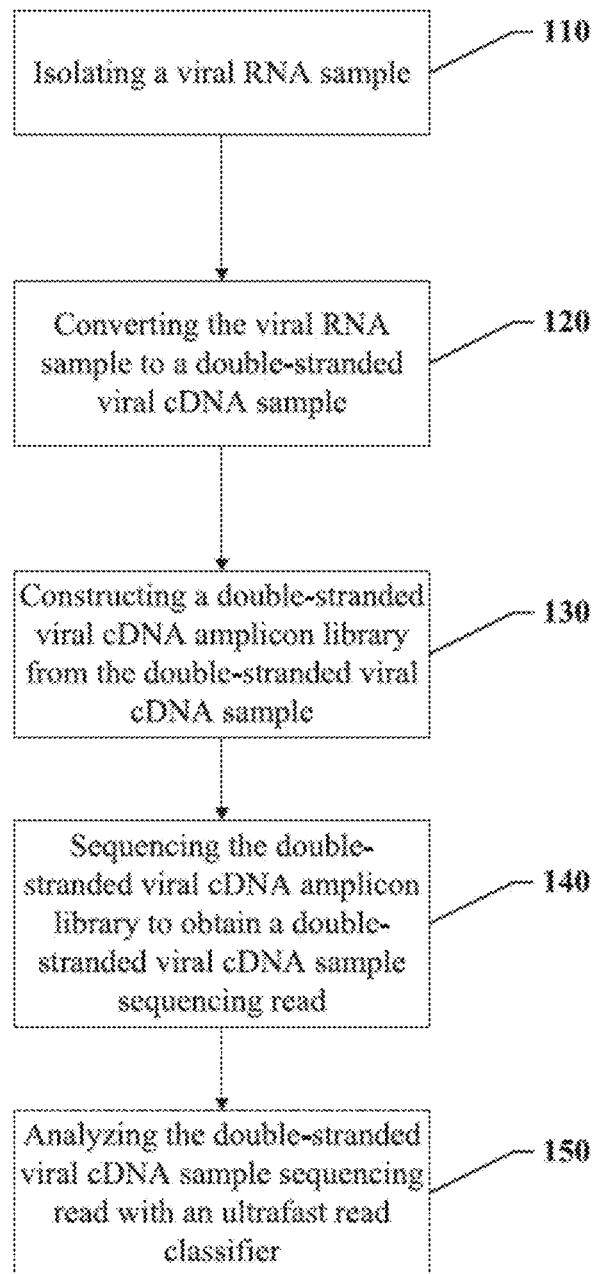
FIG. 1 illustrates a block diagram of a method for limited input whole genome sequencing of RNA viruses including an optional step of analyzing the double-stranded viral cDNA sample sequencing read with an ultrafast read classifier according to an example embodiment.

FIG. 1, for example, illustrates a block diagram of a method for limited input whole genome sequencing of RNA viruses including an optional step of analyzing the double-stranded viral cDNA sample sequencing read with an ultrafast read classifier according to an example embodiment. As shown in FIG. 1, the exemplary method includes isolating a viral RNA sample at operation 110, converting the viral RNA sample to a double-stranded viral cDNA sample at operation 120, constructing a double-stranded viral cDNA amplicon library from the double-stranded viral cDNA sample at operation 130, sequencing the double-stranded viral cDNA amplicon library to obtain a double-stranded viral cDNA sample sequencing read at operation 140, and optionally analyzing the double-stranded viral cDNA sample sequencing read with an ultrafast read classifier at operation 150.

Figure 2:
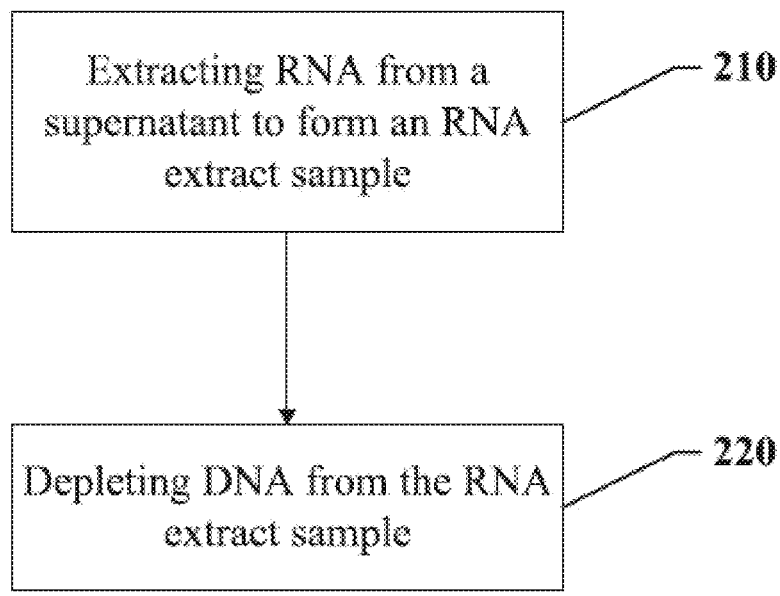
FIG. 2 illustrates a block diagram of a method of isolating a viral RNA sample according to an example embodiment.

In accordance with an example embodiment isolating the viral RNA sample may comprise, for instance, extracting RNA from a supernatant to form an RNA extract sample and depleting DNA from the RNA extract sample. FIG. 2, for example, illustrates a block diagram of a method of isolating a viral RNA sample according to an example embodiment. As shown in FIG. 2, the exemplary method includes extracting RNA from a supernatant to form an RNA extract sample at operation 210 and depleting DNA from the RNA extract sample at operation 220. In some embodiments, for instance, extracting RNA from the supernatant may comprise magnetic bead-based nucleic acid isolation. In this regard, for example, use of magnetic bead-based nucleic acid isolation may allow for increased recovery at each sample manipulation step.

In some embodiments, for instance, the supernatant may comprise an in vitro supernatant or an in vivo supernatant. In this regard, for example, an in vitro supernatant may comprise samples derived from various sources and hosts (e.g., mouse tissue culture, dog tissue culture, mosquito tissue culture, etc.). In other embodiments, for example, an in vivo supernatant may comprise (e.g., mouse feces) animal feces with high microbial content. In certain embodiments, for example, the supernatant may comprise about $10^3$ RNA viruses.

Figure 3:
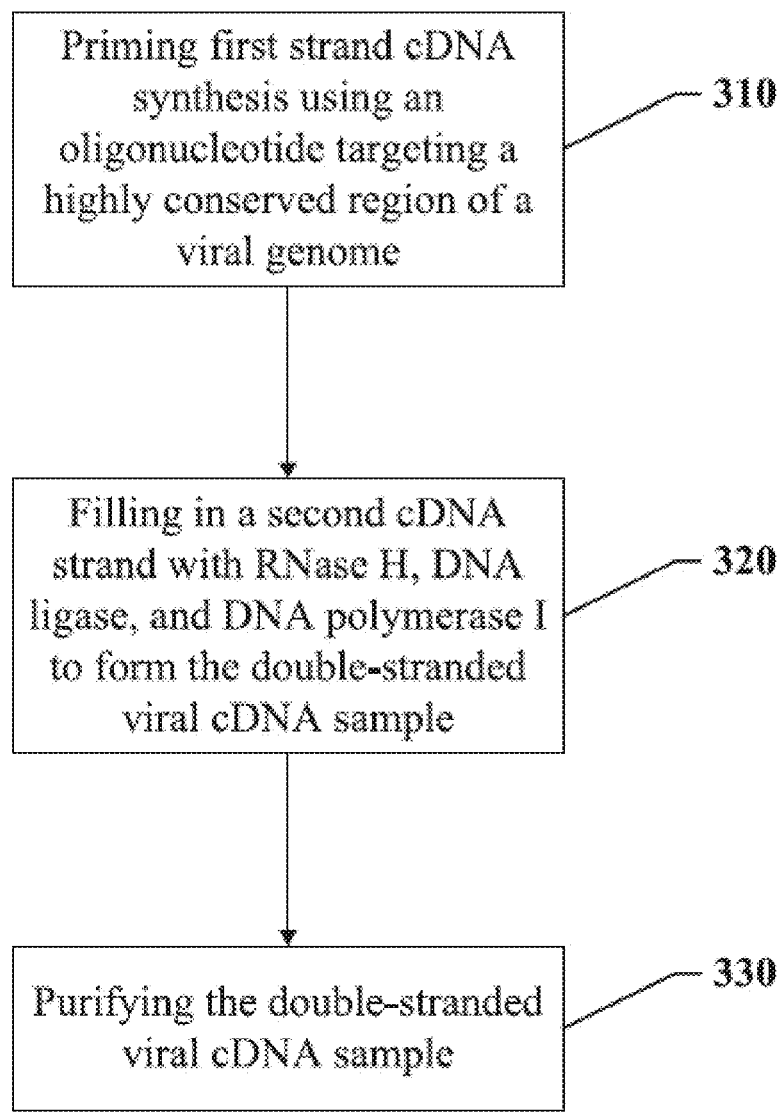
FIG. 3 illustrates a block diagram of a method of converting the viral RNA sample to a double-stranded viral cDNA sample according to an example embodiment.

According to an example embodiment, converting the viral RNA sample to the double-stranded viral cDNA sample may comprise reverse transcription of viral RNA to single stranded cDNA using an oligonucleotide primer highly specific for the viral genome of interest, synthesizing a second cDNA strand with RNase H, DNA ligase, and DNA polymerase I to form the double-stranded viral cDNA sample, and purifying the double-stranded viral cDNA sample. FIG. 3, for example, illustrates a block diagram of a method of converting the viral RNA sample to a double-stranded viral cDNA sample according to an example embodiment. As shown in FIG. 3, the exemplary method includes priming first strand cDNA synthesis with reverse transcriptase at operation 310, filling in a second cDNA strand with RNase H, DNA ligase, and DNA polymerase I to form the double-stranded viral cDNA sample at operation 320, and purifying the double-stranded viral cDNA sample at operation 330.

Many viral genomes contain highly conserved regions common to all subtypes as a means of replication, representing an ideal site for priming reverse transcription for first strand viral cDNA synthesis. As such, in some embodiments, for instance, priming first strand cDNA synthesis with reverse transcriptase may comprise direct priming from these highly conserved regions. In this regard, for example, direct priming may allow for efficient second strand synthesis by template-RNA primed fill in with DNA polymerase I and DNA ligase (e.g., *E. coli* DNA ligase). Accordingly, this minimally biased method avoids conversion of host RNA, and subsequent material may be directly input into a library preparation method (e.g., Illumina® Nextera XT and/or the like). In addition, direct viral priming of reverse transcription may obviate the need for host ribosomal RNA depletion, permitting high-depth whole genome sequencing with fewer reagents and manipulation steps and ultimately reducing time and material costs. FIG. 15, for example, illustrates improved sequencing efficiency resulting from direct primed sequencing as compared to random primed sequencing according to an example embodiment.

In accordance with an example embodiment, for instance, constructing the double-stranded viral cDNA amplicon library may comprise performing tagmentation reactions on the double-stranded viral cDNA sample to obtain the double-stranded viral cDNA amplicon library, purifying the double-stranded viral cDNA amplicon library, quantifying the double-stranded viral cDNA amplicon library, and pooling multiplexed double-stranded viral cDNA amplicon libraries. In some embodiments, for example, one set of primers may be effective in performing tagmentation reactions across different strains within a viral family. For example, the individual serotypes for DENV may be differentiated using a universal primer set for DENV. In this regard, such a universal primer set may be useful for DENV outbreaks worldwide.

Figure 4:
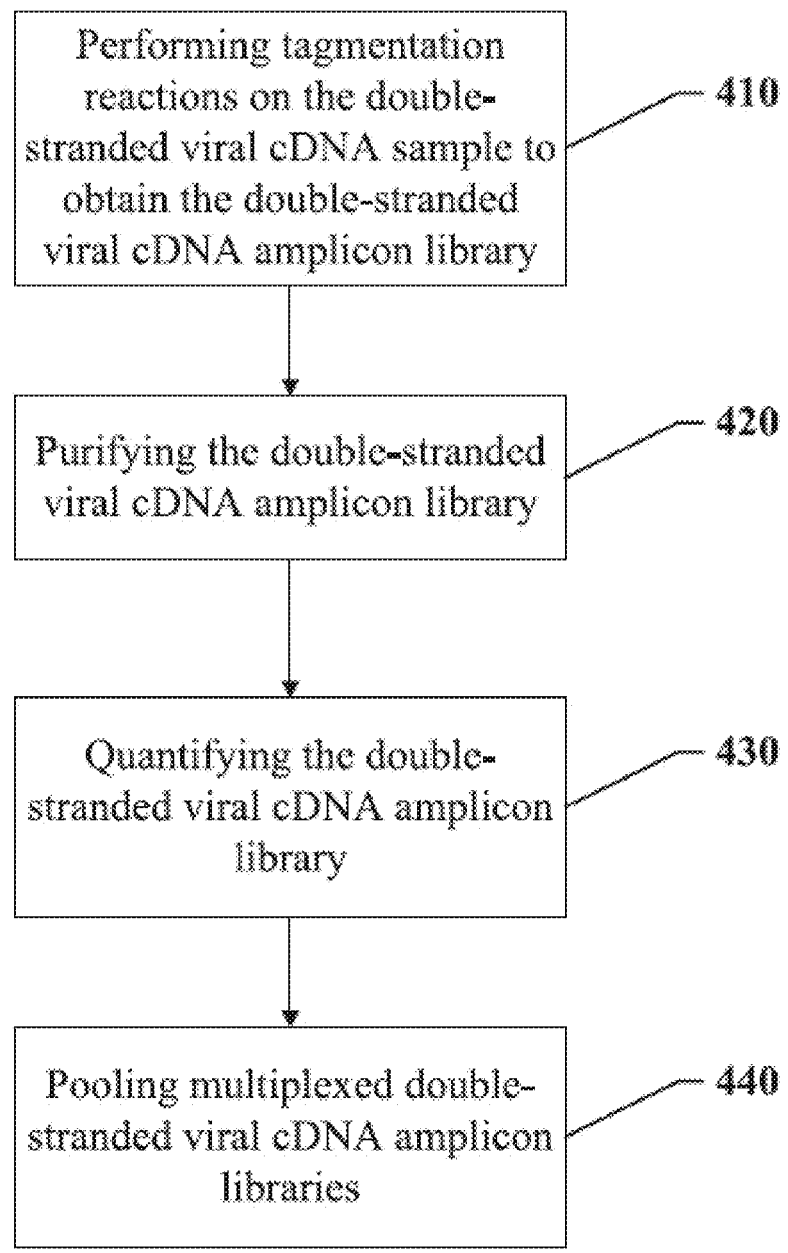
FIG. 4 illustrates a block diagram of a method of constructing a double-stranded viral cDNA amplicon library according to an example embodiment.

FIG. 4, for example, illustrates a block diagram of a method of constructing a double-stranded viral cDNA amplicon library according to an example embodiment. As shown in FIG. 4, the exemplary method includes performing tagmentation reactions on the double-stranded viral cDNA sample to obtain the double-stranded viral cDNA amplicon library at operation 410, purifying the double-stranded viral cDNA amplicon library at operation 420, quantifying the double-stranded viral cDNA amplicon library at operation 430, and pooling multiplexed double-stranded viral cDNA amplicon libraries at operation 440.

Figure 5:
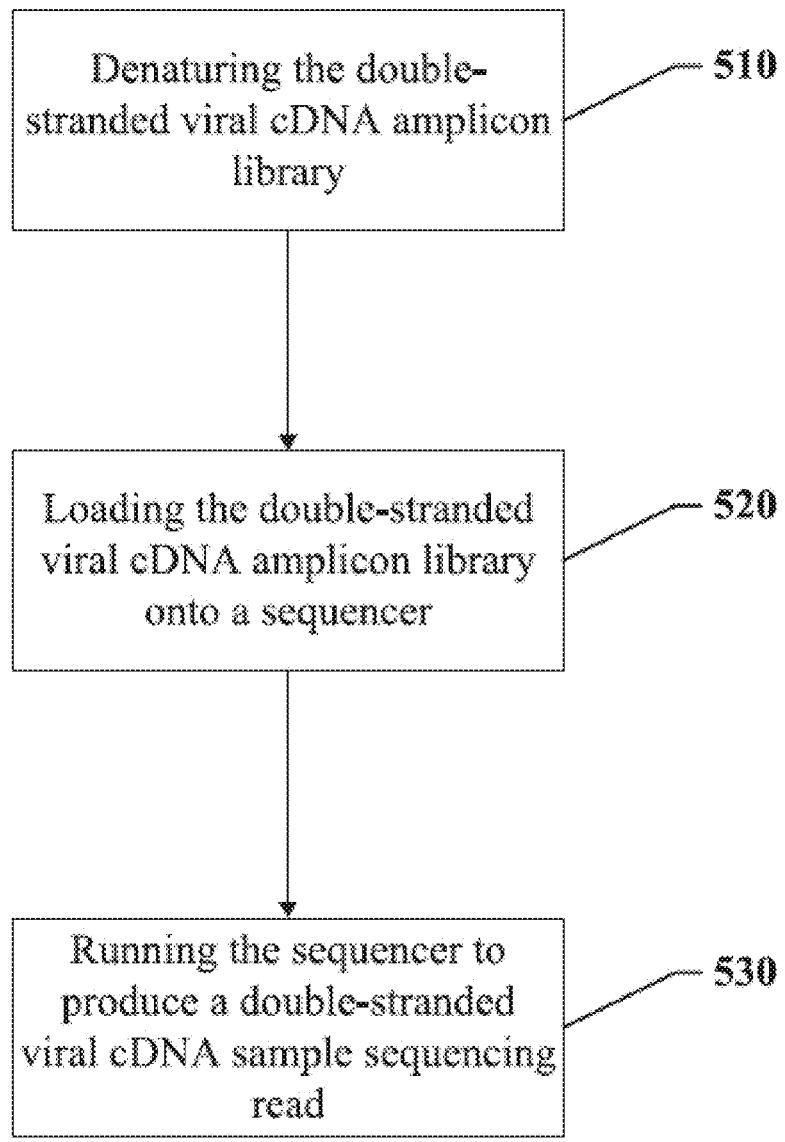
FIG. 5 illustrates a block diagram of a method of sequencing the double-stranded viral cDNA amplicon library according to an example embodiment.
Figure 6:
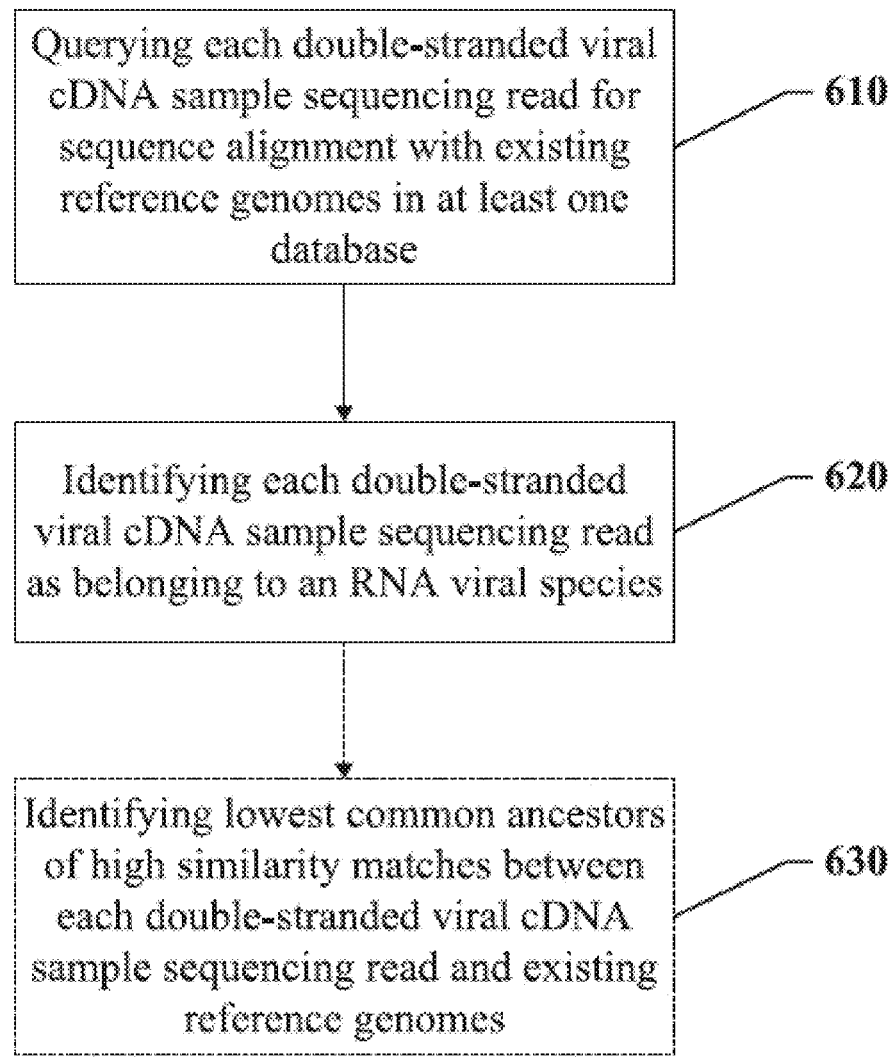
FIG. 6 illustrates a block diagram of a method of analyzing RNA virus samples via an ultrafast read classifier including an optional step of identifying lowest common ancestors of high similarity matches between each double-stranded viral cDNA sequencing read and existing reference genomes according to an example embodiment.

In accordance with an example embodiment, for instance, sequencing the double-stranded viral cDNA amplicon library may comprise denaturing the double-stranded viral cDNA amplicon library, loading the double-stranded viral cDNA amplicon library onto a sequencer (e.g., MiSeq), and running the sequencer to produce a double-stranded viral cDNA sample sequencing read. In some embodiments, for example, sequencing the double-stranded viral cDNA amplicon library may comprise sequencing from about 0.1 pg to about 10 pg converted viral genomes. In this regard, for example, the method may allow for sequencing of samples using significantly less converted viral genomes than the 1 ng typically required for Nextera XT library preparation. FIG. 5, for example, illustrates a block diagram of a method of sequencing the double-stranded viral cDNA amplicon library according to an example embodiment. As shown in FIG. 5, the exemplary method includes denaturing the double-stranded viral cDNA amplicon library at operation 510, loading the double-stranded viral cDNA amplicon library onto a sequencer at operation 520, and running the sequencer to produce a double-stranded viral cDNA sample sequencing read at operation 530.

Figure 10:
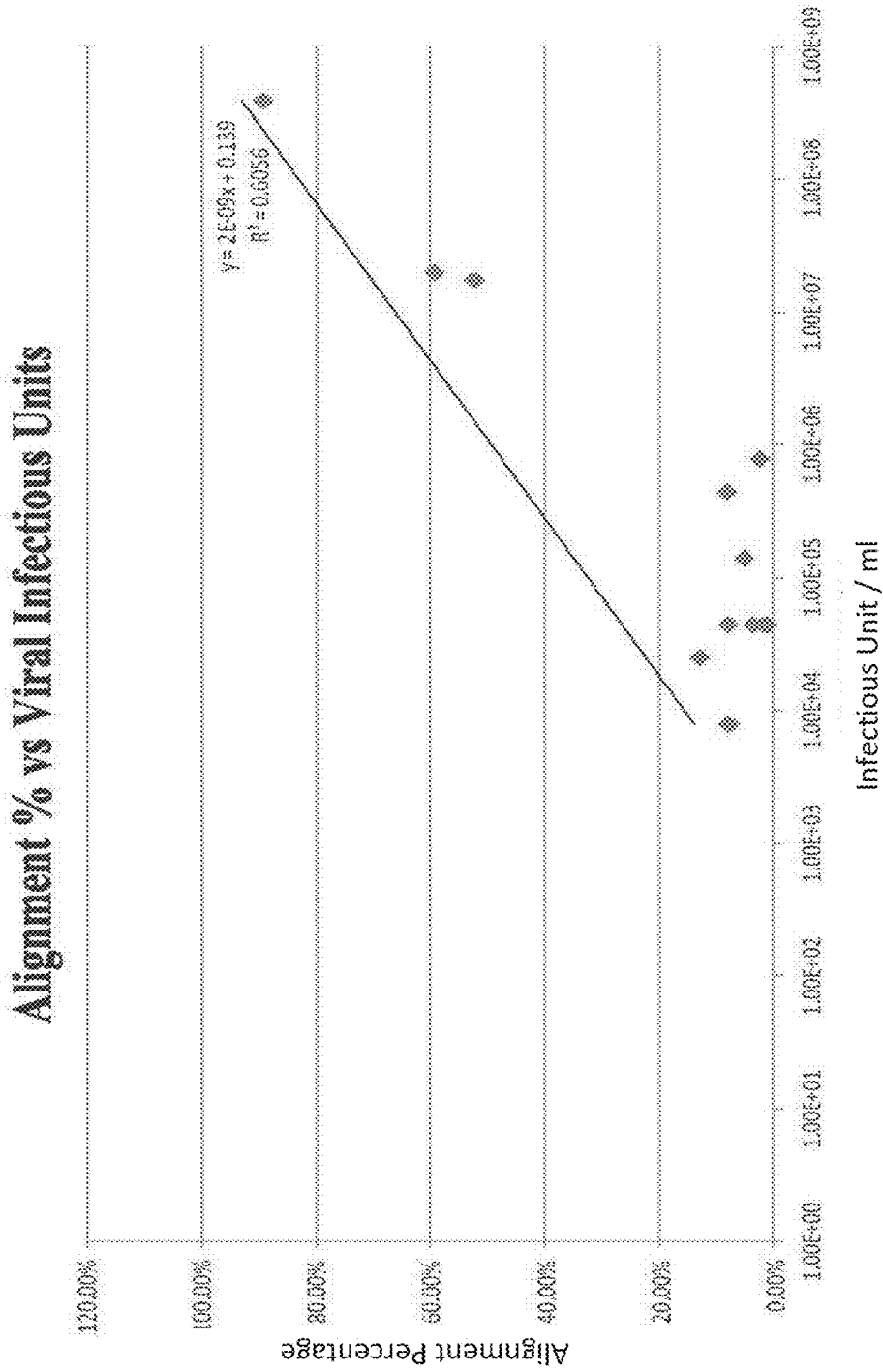
FIG. 10 illustrates the increasing sequence alignment sensitivity of next-generation sequencing in response to increased viral infectious units according to an example embodiment.

The method, according to certain embodiments, is sensitive. For example, the method may produce complete genome sequences from less than $1\times10^4$ infectious units. The method, according to an exemplary embodiment, requires very low amounts of virus input with viral loads below $1\times10^4$ PFU per mL providing significant whole genome coverage and depth. Surprisingly, for viruses that generate a ratio of approximately 100 particle: 1 PFU, for instance, the method, according to certain embodiments, may sequence $10^5$-$10^6$ genomes, which is significantly lower than the standard Illumina®-recommended input for amplification-based sequencing and four logs lower than previous amplification-free sequencing approaches. FIG. 10, for example, illustrates increasing sequence alignment sensitivity of next-generation sequencing in response to increased viral infectious units according to an example embodiment. However, as shown in FIG. 10, the method is sufficiently sensitive to produce complete genome sequences from less than $1\times10^4$ infectious units capable of being aligned with existing reference genomes. In addition, the method may be highly sensitive regardless of the source, including, for example, viruses present in culture supernatants as well as animal feces. In this regard, the low-input requirements and source-agnostic nature may make this method, according to certain embodiments, suitable for outbreaks where samples are scarce due to multiple test requirements (i.e. serology and virus culture).

Moreover, the method, according to certain embodiments, is rapid. For example, in some embodiments, the method may comprise a completion time of from about 10 hours to about 15 hours. In other embodiments, for instance, the method may comprise a completion time of from about 11 hours to about 14 hours. In further embodiments, for example, the method may comprise a completion time from about 12 hours to about 13 hours. In certain embodiments, for instance, the method may comprise a completion time of about 12.5 hours. As such, in certain embodiments, the method may comprise a completion time from at least about any of the following: 10, 11, 11.5, 12, and 12.5 hours and/or at most about 15, 14, 13.5, 13, and 12.5 hours (e.g., about 10-13 hours, about 11-12.5 hours, etc.). According to certain embodiments, for example, the method may comprise a hands-on time of from about 0.5 hours to about 5 hours. In other embodiments, for instance, the method may comprise a hands-on time of from about 1 hour to about 4 hours. In further embodiments, for example, the method may comprise a hands-on time of from about 1.5 hours to about 3 hours. In certain embodiments, for instance, the method may comprise a hands-on time of about 2.5 hours. As such, in certain embodiments, the method may comprise a hands-on time of from at least about any of the following: 0.5, 1, 1.5, 2, and 2.5 hours and/or at most about 5, 4, 3.5, 3, and 2.5 hours (e.g., about 1-2.5 hours, about 2-3 hours, etc.).

Figure 7:
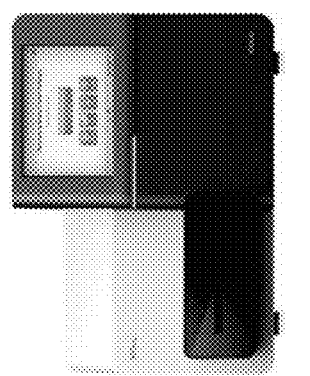
FIG. 7 illustrates a method for limited input whole genome sequencing of RNA viruses according to an example embodiment.
Figure 7:
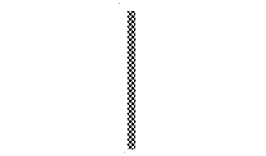
Figure 7:
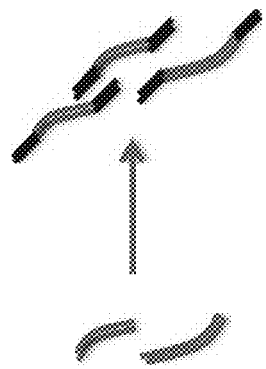
Figure 7:
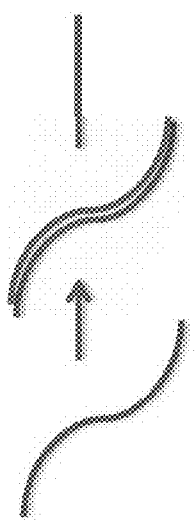
Figure 8:
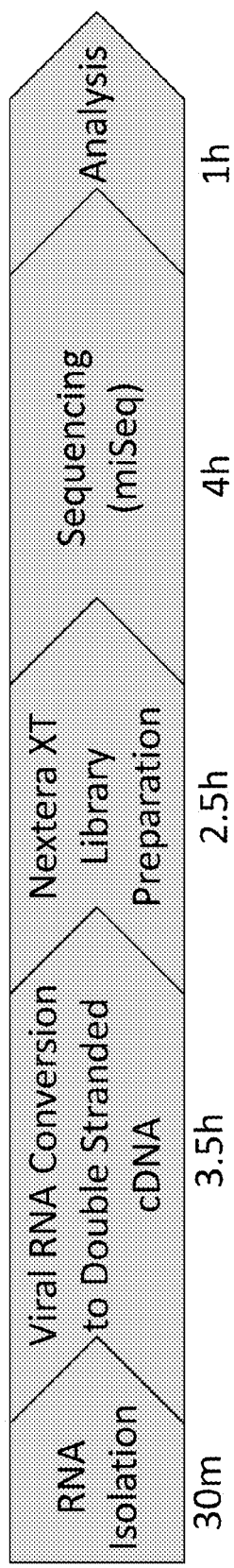
FIG. 8 illustrates the approximate time required for each step of a method for limited input whole genome sequencing of RNA viruses including an optional step of analyzing the double-stranded viral cDNA sample sequencing read with an ultrafast read classifier according to an example embodiment.
Figure 9:
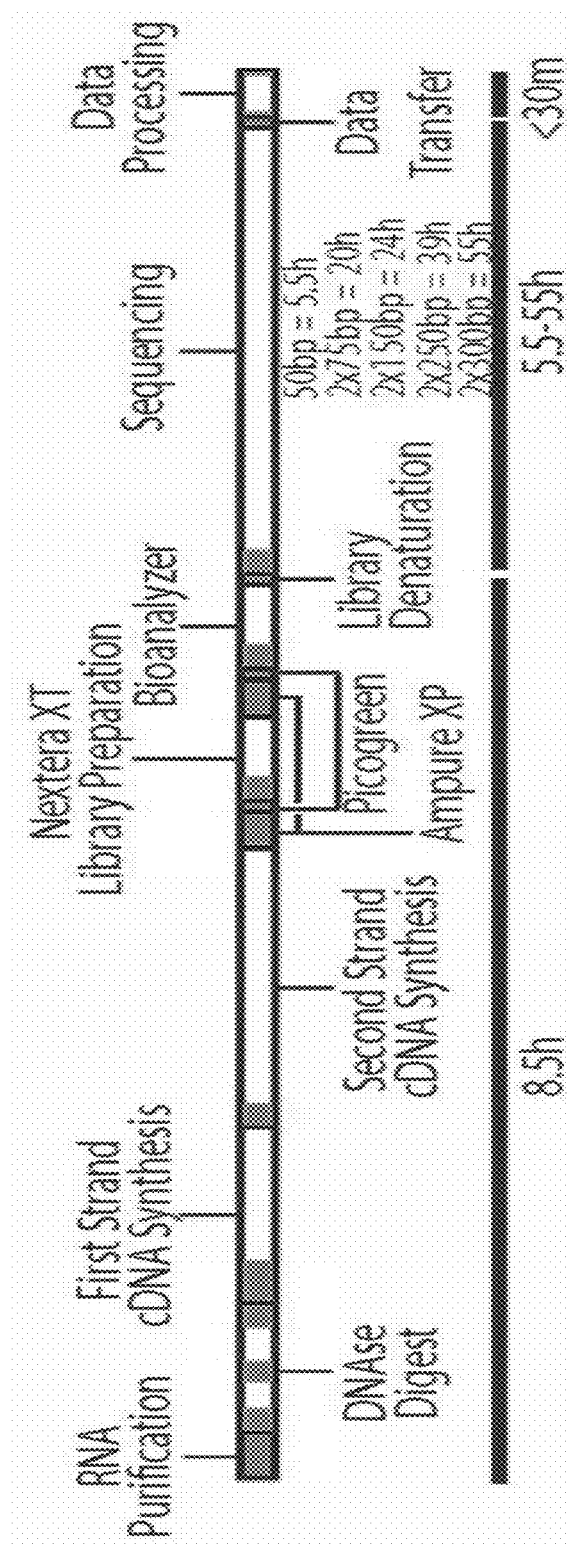
FIG. 9 illustrates rapid end-to-end sequencing and speculation of RNA viruses according to an example embodiment.

FIG. 7, for example, illustrates a method for limited input whole genome sequencing of RNA viruses according to an example embodiment. As shown in FIG. 7, a viral RNA sample is converted to a double-stranded viral cDNA sample. Next, pooled amplicon libraries are prepared from several double-stranded viral cDNA samples. These pooled (i.e. multiplexed) amplicon libraries are sequenced at the same time via one input into a sequencer. FIG. 8, for instance, illustrates the approximate time required for each step of a method for limited input whole genome sequencing of RNA viruses including an optional step of analyzing the double-stranded viral cDNA sample sequencing read with an ultrafast read classifier according to an example embodiment. As shown in FIG. 8, RNA isolation lasts for about 30 minutes, viral RNA conversion to double-stranded cDNA lasts for about 3.5 hours, Nextera XT library preparation lasts for about 2.5 hours, sequencing lasts for about 4 hours, and analysis lasts for about 1 hour. FIG. 9, for example, illustrates rapid end-to-end sequencing and speciation of RNA viruses according to an example embodiment. As shown in FIG. 9, end-to-end processing of samples may be completed in 15 hours or less. In FIG. 9, the shaded regions indicate hands on time, while the white regions indicate incubation or data processing time.

According to certain embodiments, for instance, the RNA viruses may comprise segmented genomes (e.g., Influenza A) or non-segmented genomes (e.g., dengue virus, murine norovirus (MNV-1), etc.). In some embodiments, for example, the RNA viruses may comprise at least one of double-stranded RNA viruses, positive-sense single-stranded RNA viruses, negative-sense single-stranded RNA viruses, or any combination thereof. In further embodiments, for instance, the RNA viruses may comprise positive-sense single-stranded RNA viruses with polyadenylated 3' ends (e.g., MNV-1). In other embodiments, for example, the RNA viruses may comprise positive-sense single-stranded RNA viruses without polyadenylation (e.g., DENV serotypes 1-4). In certain embodiments, for instance, the RNA viruses may comprise negative-sense single-stranded segmented RNA viruses (e.g., Influenza A).

As such, in accordance with certain embodiments, the RNA viruses may comprise RNA viruses including, but not limited to, flaviviruses, alphaviruses, bromoviruses, arteriviruses, aphthoviruses, rhinoviruses, hepatoviruses, cardioviruses, cosaviruses, dicipiviruses, erboviruses, kobuviruses, megriviruses, parechoviruses, pisceviruses, saliviruses, sapeloviruses, senecaviruses, teschoviruses, tremoviruses, potyviruses, coronaviruses, noroviruses, orthomyxoviruses, rotaviruses, picobirnaviruses, enteroviruses, bymoviruses, comoviruses, nepoviruses, nodaviruses, picornaviruses, sobemoviruses, luteoviruses, carmoviruses, dianthoviruses, pestiviruses, tombusviruses, single-stranded RNA bacteriophages, carlaviruses, furoviruses, hordeiviruses, potexviruses, rubiviruses, tobraviruses, tricornaviruses, tymoviruses, and/or the like. In further embodiments, for example, the RNA viruses may comprise RNA viruses including, but not limited to, dengue virus (e.g., DENV1, DENV2, DENV3, DENV4), West Nile virus, absettarov virus, alkhurma virus, deer tick virus, gadgets gully virus, kadam virus, karshi virus, kyasanur forest disease virus, Langat virus, louping ill virus, omsk hemorrhagic fever virus, powassan virus, royal farm virus, sokuluk virus, tick-borne encephalitis virus, Turkish sheep encephalitis virus, kama virus, meaban virus, Saumarez Reef virus, tyuleniy virus, Aedes flavivirus, barkedji virus, calbertado virus, cell fusing agent virus, chaoyang virus, culex flavivirus, culex theileri flavivirus, donggang virus, ilomantsi virus, Kamiti River virus, lammi virus, marisma mosquito virus, nakiwogo virus, nhumirim virus, nounane virus, Spanish culex flavivirus, Spanish ochlerotatus flavivirus, quang binh virus, aroa virus, bussuquara virus, kedougou virus, cacipacore virus, koutango virus, ilheus virus, Japanese encephalitis virus, Murray Valley encephalitis virus, alfuy virus, rocio virus, St. Louis encephalitis virus, usutu virus, yaounde virus, kokobera virus, bagaza virus, baiyangdian virus, duck egg drop syndrome virus, Jiangsu virus, Israel turkey meningoencephalomyelitis virus, ntaya virus, tembusu virus, zika virus, banzi virus, bouboui virus, edge hill virus, jugra virus, saboya virus, sepik virus, Uganda S virus, wesselsbron virus, yellow fever virus, Entebbe bat virus, yokose virus, apoi virus, vowbone ridge virus, Jutiapa virus, modoc virus, sal vieja virus, san perlita virus, bukalasa bat virus, Carey Island virus, Dakar bat virus, Montana myotis leukoencephalitis virus, Phnom Penh bat virus, Rio Bravo virus, soybean cyst nematode virus 5, Aedes cinereus flavivirus, Aedes vexans flavivirus, Coxsackievirus, echovirus, Enterovirus A, Enterovirus B, Enterovirus C, Enterovirus D, Enterovirus E, Enterovirus F, Enterovirus G, Enterovirus H, Enterovirus J, Rhinovirus A, Rhinovirus B, Rhinovirus C, poliovirus, bovine viral diarrhea virus, sindbis virus, hepatitis C, Barmah Forest virus, eastern equine encephalitis virus, Middelburg virus, ndumu virus, bebaru virus, chikungunya virus, mayaro virus, una virus, o'nyong nyong virus, Igbo-Ora virus, Ross River virus, getah virus, sagiyama virus, Semliki Forest virus, metrivirus, cabassou virus, Everglades virus, mosso das pedras virus, mucambo virus, paramana virus, pixuna virus, Rio Negro virus, trocara virus, Bijou Bridge virus, Venezuelan equine encephalitis virus, aura virus, babanki virus, kyzylagach virus, ockelbo virus, whataroa virus, Buggy Creek virus, Fort Morgan virus, Highlands J virus, western equine encephalitis virus, salmon pancreatic disease virus, sleeping disease virus, southern elephant seal virus, tonate virus, Brome mosaic virus, equine arteritis virus, foot-and-mouth disease virus, bovine rhinitis A virus, bovine rhinitis B virus, equine rhinitis A virus, aquamavirus A, duck hepatitis A virus, encephalomyocarditis virus, theilovirus, cosavirus A, cadicivirus A, equine rhinitis B virus, hepatitis A virus, aichivirus A, aichivirus B, aichivirus C, melegrivirus A, human parechovirus, Ljungan virus, fathead minnow picornavirus, salivirus A, porcine sapelovirus, simian sapelovirus, avian sapelovirus, Seneca Valley virus, porcine teschovirus, avian encephalomyelitis virus, potato virus A, SARS, Human coronavirus 229E, Human coronavirus OC43, New Haven coronavirus, Human coronavirus HKU1, Middle East respiratory syndrome coronavirus, infectious bronchitis virus, porcine coronavirus, bovine coronavirus, feline coronavirus, canine coronavirus, turkey coronavirus, ferret enteric coronavirus, ferret systemic coronavirus, pantropic canine coronavirus, porcine epidemic diarrhea virus, Ebola virus, measles virus, Influenza virus A, Influenza virus B, Influenza virus C, isavirus, thogotovirus, quaranjavirus, Norwalk virus, Hawaii virus, Snow Mountain virus, Mexico virus, Desert Shield virus, Southampton virus, Lordsdale virus, Wilkinson virus, bluetongue virus, hepatitis E virus, apple chlorotic leaf spot virus, beet yellows virus, Rubella virus, Marburg virus, Mumps virus, Nipah virus, Hendra virus, RSV, NDV, Rabies virus, Nyavirus, Lassa virus, Hantavirus, Crimean-Congo hemorrhagic fever, hepatitis D virus, Nyamanini virus, Midway virus, and/or the like.

Moreover, the method may comprise using a pool of primers designed for a variety of suspected viral pathogens in order to, for example, sequence unknown virus samples. In such embodiments, for instance, the method may comprise highly conserved priming approaches or degenerate priming approaches. In addition, in some embodiments, for example, using a pool of primers may comprise identifying co-infections with multiple viruses within a sample. In further embodiments, for instance, the method may comprise alternative primer design tools and algorithms for identifying ideal priming regions in variable genomes of targeted viruses.

In another aspect, a method of analyzing RNA virus samples via an ultrafast read classifier (i.e. Kraken) is provided. In general, the method of analyzing RNA virus samples via an ultrafast read classifier (i.e. Kraken), according to certain embodiments, comprises querying each double-stranded viral cDNA sequencing read for sequence alignment with existing reference genomes in at least one database and identifying each double-stranded viral cDNA sequencing read as belong to an RNA viral species. In this regard, methods according to example embodiments, for instance, may minimize the introduction of sample handling error.

In some embodiments, for instance, the method may further comprise identifying lowest common ancestors of high similarity matches between each double-stranded viral cDNA sequencing read and existing reference genomes. According to certain embodiments, for example, Kraken may assign each sequencing read a lowest common ancestor based on taxonomic classification when an exact 31-basepair match to a reference genome is identified. In this regard, this k-mer matching approach has been shown to be similar in specificity to BLAST, and its designs is specifically suited to metagenomic data analysis without relying on traditional alignment tools such as BWA, Bowtie, SNAP, or others. As such, in certain embodiments, for example, identifying lowest common ancestors may be used to determine downstream analysis requirements (e.g., choices for reference alignment, subsequent consensus sequence generation, etc.). Importantly, in certain embodiments, for instance, analysis with Kraken is extremely rapid, processing more than one million sequencing reads per minute. In certain embodiments, for example, the ultrafast read classifier (i.e. Kraken) may analyze from about 3 million to about 4 million double-stranded viral cDNA sequencing reads in from about 1 minute to about 5 minutes.

FIG. 6, for example, illustrates a block diagram of a method of analyzing RNA virus samples via an ultrafast read classifier including an optional step of identifying lowest common ancestors of high similarity matches between each double-stranded viral cDNA sequencing read and existing reference genomes according to an example embodiment. As shown in FIG. 6, the exemplary method includes querying each double-stranded viral cDNA sample sequencing read for sequence alignment with existing reference genomes in at least one database at operation 610, identifying each double-stranded viral cDNA sample sequencing read as belonging to an RNA viral species at operation 620, and an optional step of identifying lowest common ancestors of high similarity matches between each double-stranded viral cDNA sample sequencing read and existing reference genomes at operation 630.

According to certain embodiments, for example, the method may have a sequence alignment with existing reference genomes from about 90% to about 100%. In other embodiments, for instance, the method may have a sequence alignment with existing reference genomes from about 95% to about 100%. In further embodiments, for example, the method may have a sequence alignment with existing reference genomes from about 99% to about 100%. As such, in certain embodiments, the method may have a sequence alignment with existing reference genomes from at least about any of the following: 80, 85, 90, 95, and 99% and/or at most about 100% (e.g., 95-100%, 99-100%, etc.).

Universal sample preparation protocols may present bioinformatic challenges when a sample does not align to an anticipated reference sequence. As such, in order to bypass troubleshooting necessary for de novo assembly algorithms such as data downsampling, removal of host sequences, and high computational resources, in some embodiments, for instance, the at least one database may comprise at least one of a full metagenomics implementation, a pan-virus implementation, a virus-specific implementation, or any combination thereof. These databases are relatively small when restricted to viruses or Influenza subtypes, and analysis may be conducted with modest computing power (e.g., a laptop computer). This identification step accelerates reference-based assembly, allowing for complete end-to-end data processing with very little computational infrastructure. In some embodiments, for instance, the full metagenomics implementation may comprise all genomes present in a given Kraken database. According to certain embodiments, for example, the pan-virus implementation may comprise all 5,264 virus genomes present in the NCBI reference sequence database (http://www.ncbi.nlm.nih.gov/refseq/). In other embodiments, for instance, the virus-specific implementation may comprise all complete Influenza A genome segments maintained in the Influenza Research Database (fludb.org). As such, the Influenza A-specific implementation may comprise about 226,482 sequences representing about 125 subtypes organized in taxonomy according to, for example, genome segment, subtype, year, and strain. FIG. 14, for example, illustrates a database for an Influenza A-specific implementation of the ultrafast read classifier according to an example embodiment.

In an example embodiment, the ultrafast read classifier 40 may be any means such as a device or circuitry embodied in either hardware, or a combination of hardware and software that is configured to execute (or provide instructions for execution of) analysis of a double-stranded viral cDNA sample sequencing read. In this regard, the ultrafast read classifier 40 is configured to compare a double-stranded viral cDNA sequencing read with existing reference genomes stored in various databases comprising at least one of the implementations discussed herein. FIG. 16 illustrates a block diagram of the ultrafast read classifier 40 in accordance with an example embodiment. In this regard, as shown in FIG. 4, the ultrafast read classifier 40 may include processing circuitry 41 that may be configured to interface with, control or otherwise coordinate the operations of various components or modules described herein in connection with analyzing a double-stranded viral cDNA sample sequencing read as described herein.

In some embodiments, the processing circuitry 41 may be embodied as a chip or chip set. In other words, the processing circuitry 41 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The processing circuitry 41 may therefore, in some cases, be configured to implement an embodiment of the present invention on a single chip or as a single "system on a chip." As such, in some cases, a chip or chipset may constitute means for performing one or more operations for providing the functionalities described herein.

In an example embodiment, the processing circuitry 41 may include one or more instances of a processor 42 and memory 43 that may be in communication with or otherwise control a user interface 44. As such, the processing circuitry 41 may be embodied as a circuit chip (e.g., an integrated circuit chip) configured (e.g., with hardware, software or a combination of hardware and software) to perform operations described herein.

The user interface 44 may include one or more interface mechanisms or devices for enabling communication with a user (e.g., a laptop computer). In some cases, the user interface 44 may be any means such as a device or circuitry embodied in either hardware, or a combination of hardware and software that is configured to receive and/or transmit data from/to devices or components in communication with the processing circuitry 41 via internal and/or external communication mechanisms. Accordingly, for example, the user interface 44 may further include wired and/or wireless communication equipment for at least communicating between a user and the ultrafast read classifier 40, and/or other components or modules described herein.

The processor 42 may be embodied in a number of different ways. For example, the processor 42 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 42 may be configured to execute instructions stored in the memory 43 or otherwise accessible to the processor 42. As such, whether configured by hardware or by a combination of hardware and software, the processor 42 may represent an entity (e.g., physically embodied in circuitry—in the form of processing circuitry 41) capable of performing operations according to embodiments of the present invention while configured accordingly. Thus, for example, when the processor 42 is embodied as an ASIC, FPGA or the like, the processor 42 may be specifically configured hardware for conducting the operations described herein. Alternatively, as another example, when the processor 42 is embodied as an executor of software instructions, the instructions may specifically configure the processor 42 to perform the operations described herein in reference to execution of an example embodiment.

In an exemplary embodiment, the memory 43 may include one or more non-transitory memory devices such as, for example, volatile and/or non-volatile memory that may be either fixed or removable. The memory 43 may be configured to store information, data, applications, instructions or the like for enabling the processing circuitry 41 to carry out various functions in accordance with exemplary embodiments of the present invention. For example, the memory 43 may be configured to buffer input data for processing by the processor 42. Additionally or alternatively, the memory 43 may be configured to store instructions for execution by the processor 42. As yet another alternative or additional capability, the memory 43 may include one or more databases that may store or buffer a variety of data sets or tables useful for operation of the modules described below and/or the processing circuitry 41. Among the contents of the memory 43, applications or instruction sets may be stored for execution by the processor 42 in order to carry out the functionality associated with each respective application or instruction set. In particular, the memory 43 may store executable instructions that enable the computational power of the processing circuitry 41 to be employed to improve the functioning of the ultrafast read classifier 40 as described herein. As such, the improved operation of the computational components of the ultrafast read classifier 40 transforms the ultrafast read classifier 40 into a more capable tool for analysis of double-stranded viral cDNA sample sequencing reads as described herein.

In some embodiments, for instance, the ultrafast read classifier (i.e. Kraken) may identify nearest neighbor RNA viruses in from about 1 minute to about 15 minutes. In this regard, Kraken may identify both the majority and minority virus genetic species, including rare populations, present in a sample.

As such, methods according to example embodiments demonstrate a rapid turnaround approach for whole-genome sequencing and bioinformatic speciation of RNA viruses from low quantity samples and with limited manipulation. In this regard, methods according to example embodiments create inexpensive, rapid, and low-input pipelines for high throughput, whole genome virus sequencing and speciation. This minimally biased direct priming method minimizes co-sequencing of extraneous host DNA and ribosomal RNA, and excludes error prone amplification steps. Further, the platform may be applied to all RNA virus genetic organizations. The speed and sensitivity of the process pipeline represent a significant advance over current methodologies, and may be useful in sequencing suspected, but unidentified, virus infections as well as studying virus evolution during outbreak events, particularly from very low quantity viral pathogen samples.

EXAMPLES

The present disclosure is further illustrated by the following examples, which in no way should be construed as being limiting. That is, the specific features described in the following examples are merely illustrative, and not limiting.

Virus Samples

Plaque-purified MNV-1 clone (GV/MNV-1/2002/USA) MNV-1.CW3 was produced from RAW264.7 cells Influenza virus A/H1N1 (A/Giessen/6/2009) was produced in MDCK cells. Dengue virus serotype-1 (Hawaii strain), -2 (V2618 strain), -3 (H87 strain), and -4 (H241 strain) were produced in C6/36 mosquito cells. For all samples, virus titer was determined by plaque assay or by tissue culture infectious dose (TCID) assay.

RNA Extraction

Tissue culture (MNV-1, DENV, and Influenza) or stool supernatants (MNV-1) were centrifuged for five minutes at 16,000×g to remove cell and other debris. Clarified supernatants were purified per manufacturer recommendations with the Ambion® MagMAX™ Viral RNA purification reagent, with the only protocol modification being omission of carrier RNA to the viral lysis enhancer reagent. Samples were resuspended in 20 uL of supplied RNase free elution buffer.

DNA Removal

Ambion® TURBO™ DNA-free reagent (Life Technologies) was used to deplete genomic DNA. Manufacturer instructions for stringent DNase treatments were followed, adding 2 U of enzyme at the beginning of treatment and after 30 minutes at 37° C. Total duration of DNA depletion was one hour, after which DNase inactivation reagent was added at 0.2 volumes.

Primer Design

MNV-1 primers were designed using Primer 3 against NC_008311. For degenerate DENV primers, progressive alignment of DENV genomes M93130.1, EU848545.1, M84727.1, and AY947539.1 was performed using CLC Sequence Viewer 6.7.1. Reverse priming sites were selected for regions containing 80% or greater similarity along 20 bp regions. Tailed primers containing Nextera XT insertion sites were designed using information from the Illumina® Customer Sequence Letter regarding adapter sequences.

Preparation of Double-Stranded Viral cDNA

Reverse transcription of viral RNA was carried out with Superscript® III (Invitrogen™) per manufacturer instructions for gene specific priming of low input samples, using pooled primers for each virus, as shown in Table 1 below. Briefly, primers and dNTPs were added to RNA and annealed by heating to 65° C. for five minutes, then allowed to return to 4° C. for five minutes. 400 U of enzyme was then used in a total reaction volume of 40 uL, and reverse transcription was carried out at 50° C. Upon completion, second strand synthesis was carried out at 16° C. for 2.5 hours using NEBNext® mRNA Second Strand Synthesis reagent (New England Biolabs), which is comprised of *E. coli* DNA Pol I, *E. coli* DNA ligase, and RNase H, in a total volume of 80 uL.

Double-stranded viral cDNA was purified using one volume of Agencourt® AMPure XP per manufacturer instructions (Beckman Coulter). Once beads were completely dry, samples were eluted in 7.5 uL of nuclease free water for five minutes prior to collection. One microliter was used for quantification with the Invitrogen™ High Sensitivity Qubit™ reagent according to manufacturer instructions.

Nextera XT Sequencing Library Construction

Nextera XT library preparation was carried out per manufacturer instructions (Illumina®). For samples that resulted in less than one nanogram or unquantifiable amounts of DNA by picogreen, library preparation was carried out with the maximum amount of DNA available in 5 uL. After tagmentation and addition of sequencing adapters by 12 cycles of PCR, samples were purified with one volume of Agencourt® AMPure XP and eluted in 10 uL of nuclease free water. One microliter of the resulting library was then used for quantification with Invitrogen™ High Sensitivity Qubit™ reagents, and multiplexed libraries were then pooled equi-mass, assuming an even size distribution between samples.

Molar concentration of the final pooled libraries was determined by triplicate measurements of mass with High Sensitivity Qubit™ reagents and singular measurement of size using High Sensitivity DNA reagents on an Agilent Bioanalyzer. Samples were denatured per manufacturer instructions and loaded onto an Illumina® MiSeq (control software v2.3.03) at a final concentration of 10 pM. If manufacturer instructions for denaturing pooled libraries using NaOH would result in a final loading concentration lower than 10 pM, an alternate denaturing protocol was used. Rather than denaturing in 0.2M NaOH, the total amount of library needed for 10 pM in 600 uL was denatured with 2 uL 1M NaOH for five minutes, placed on ice for two minutes, and 2 uL 1M HCl was used to neutralize NaOH prior to addition of the remaining volume of HT1.

Data Quality Filtering and Reference Alignment

Resulting reads were trimmed to a minimum quality threshold of Q30 within a 20 bp window of both the 5' and 3' ends of reads using the Galaxy NGS fastq_trimmer_by_quality tool, calling arguments: -f 'sanger'-s '20'-t '3'-e '53'-a 'min'-x '0'-c '>='-q '30.0'.

Quality filtered reads were removed if their mate did not pass the quality filtering step using a custom script, available at github.com/tmehoke/vrnaseq-tools, then aligned to their anticipated reference genome using Bowtie2 through Galaxy NGS, implementing the command: bowtie2-p 32-x [bowtie2_index]-1 [fastq1]-2 [fastq2]-S [output_filename]-I20-X 700|samtools view -Su-|samtools sort -o-->[sorted_bam_file]. Resulting .bam files were then analyzed with Qualimap bamQC v0.8 [40] to determine total reads aligned, read depth, mean coverage, and library insert size using the command: qualimap bamqc-barn [sorted_bam_file]-c-nw 400-hm 3. Resulting depth of coverage and library insert size data were and plotted using GraphPad Prism version 5.0f.

Viral Speciation with Kraken

Properly paired quality filtered reads were classified using Kraken version 0.10.5-beta against a standard database, including all bacteria and viruses, as well as a custom database containing all complete virus genomes (both DNA and RNA, available from ftp.ncbi.nih.gov/genomes as of Mar. 10, 2014) using the command: kraken--db [kraken_database]--threads 64--output [output_file]--fastq-input--paired [.fastq1][.fastq2]. Similarly, a second custom database was constructed containing all complete Influenza A segments from the Influenza Research Database (fludb.org). Influenza A speciation was subset by individual genome segments (HA, NA, etc.), followed by subtype (H1, H3, etc.), then the year isolated, and finally by strain.

Use of Nextera XT for Minimal Input RNA Virus Sequencing

Samples of murine norovirus (MNV-1)-infected culture supernatants were prepared for amplicon deep sequencing with and without second strand fill-in during cDNA synthesis, using virus-specific primers tiled across the genome to avoid conversion of host RNA, as shown in Table 1.

TABLE 1

Reverse Transcription Primers for Direct Viral Priming

| Target | Primer Name | Sequence |
|---|---|---|
| MNV-1 | PT-00107 | AGCCGATCACAGGCTCCTTGGC |
|  | PT-00108 | CCATCGGCCATAAGAGGGCTGGC |
|  | PT-00109 | ACGCACTTCCTCAACTCAGCCG |
|  | PT-00110 | GGCCATGCTGATCCTGGCCA |
|  | PT-00111 | CCACCAGGATGCCATCCGAGA |
|  | PT-00112 | GTCGACATCAGCGCGTGGTATGA |
|  | PT-00113 | CAACAGGGTGGGCACCACGTC |
|  | PT-00114 | CAACAACAGGGCTCTCAGCATAAACCAG |
| Universal DENV | PT-00062 | CCTTCCACRAARTCTCTRTT |
|  | PT-00063 | ATTTCCATSCCRTACCARCA |
|  | PT-00064 | ACRTGCCACATTGTRTGRAA |
|  | PT-00065 | GACCAKCCWCCTCTBCCRCA |
|  | PT-00066 | GCTCCMARCCACATGTACCA |
|  | PT-00068[1] | *GTCTCGTGGGCTCGGAGATGTGTATAAGA GACAGGGGAGGGGTCTCCTCTAACC* |
| Universal Influenza A | PT-00076[1] | *GTCTCGTGGGCTCGGAGATGTGTATAAGA GACAGAGTAGAAACAAGG* |

[1]These primers include the full Nextera XT insertion sequence (italics) normally added during library preparation.

Figure 12A:
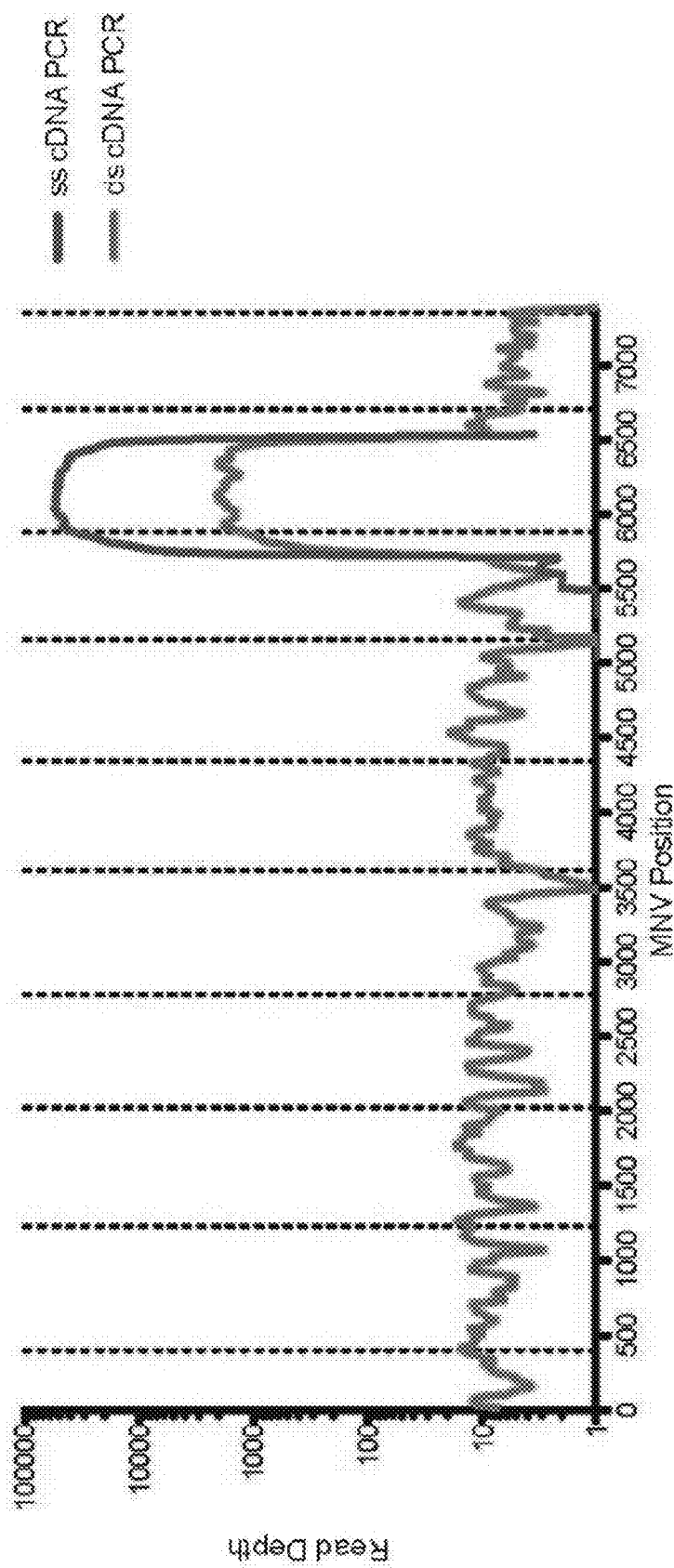

MNV-1 is a small, positive-strand RNA virus with a 3' poly-A tail that made it an attractive candidate for sequencing protocol development. Amplicon libraries produced from single-stranded cDNA provided significant coverage across the amplicon, while sibling samples undergoing second strand fill-in prior to PCR amplification additionally showed low coverage across the entire viral genome. FIG. 12, as represented by FIGS. 12A-12D, illustrates validation of double-stranded MNV-1 cDNA for use with amplicon library preparation according to an example embodiment. For example, as shown in FIG. 12A, double-stranded cDNA was validated as suitable input into Nextera XT library preparation by direct priming of MNV-1 from culture supernatant with and without second strand fill in prior to PCR amplification. In FIG. 12A, hash lines indicate virus specific reverse transcription priming sites. Direct sequencing of double-stranded viral cDNA generated from $3.1 \times 10^6$ PFU of MNV-1 from culture supernatant resulted in a final library containing more than 96% viral content and covering 100% of the reference genome, as shown in Table 2.

Figure 12B:
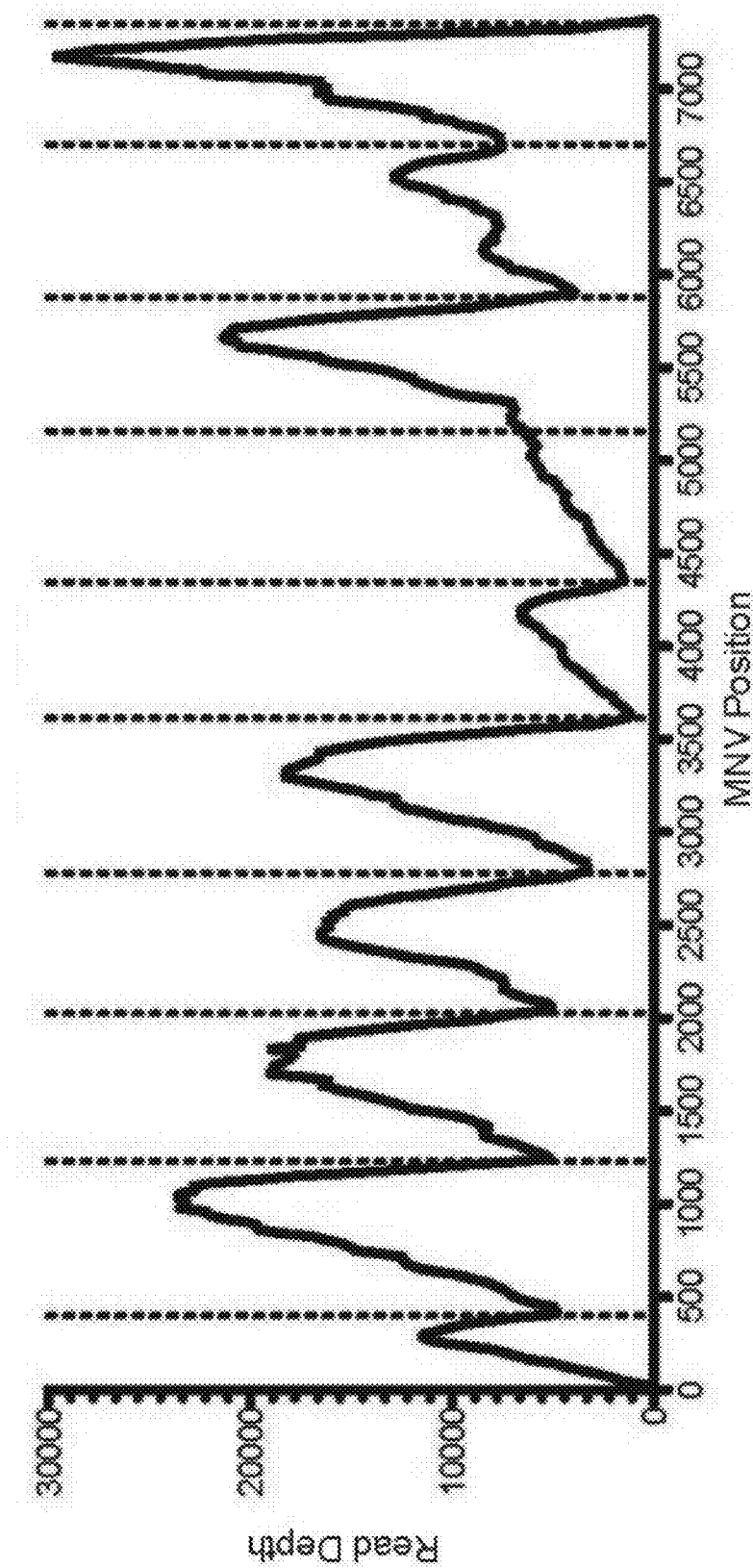

Depth of coverage remained consistently high over the entire reference with peaks and valleys observable from 3' to 5', indicating successful initiation of reverse transcription and the gradual falling off of reverse transcriptase between priming events. FIG. 12B illustrates successful preparation of Nextera XT libraries directly from double-stranded viral cDNA using culture supernatant.

Validation of Protocol on Animal Samples

Figure 12C:
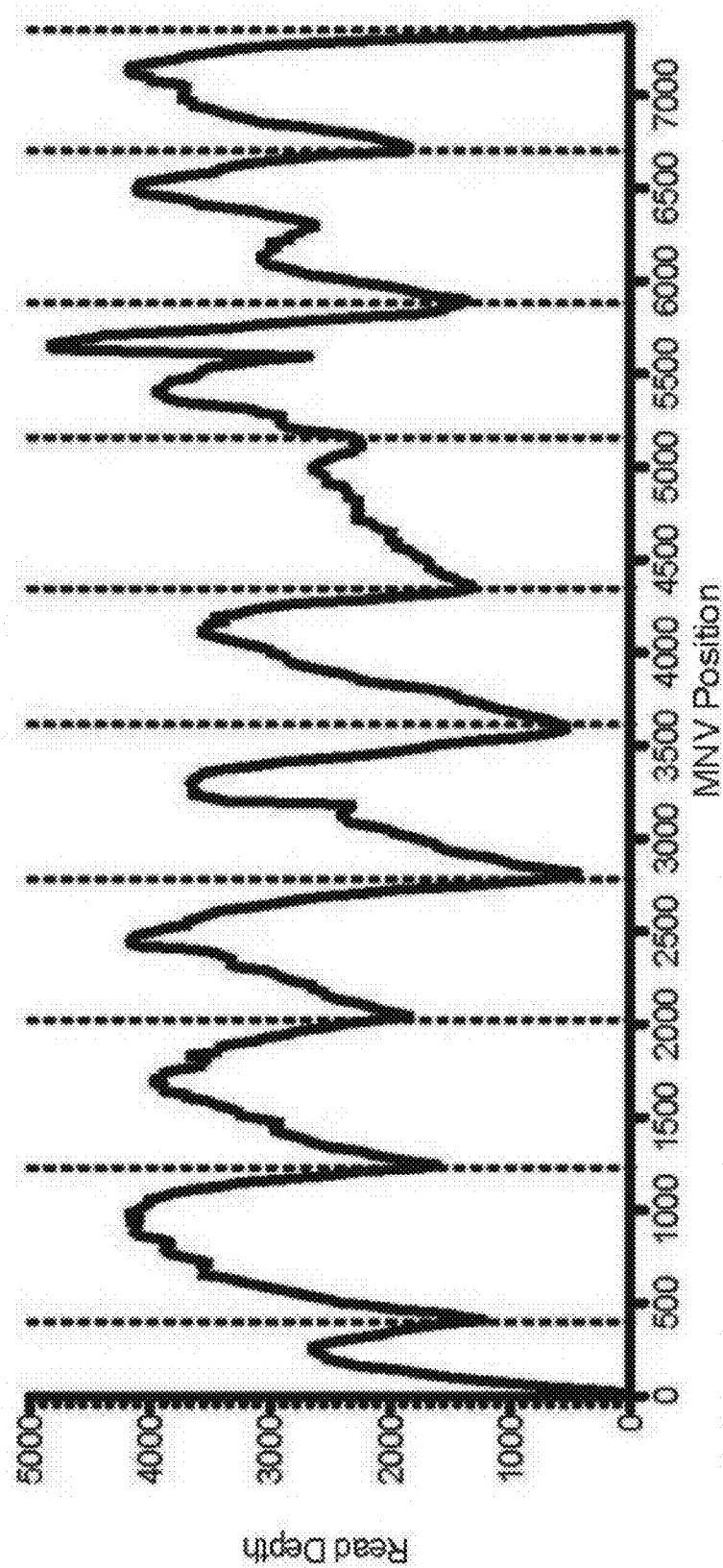
Figure 12D:
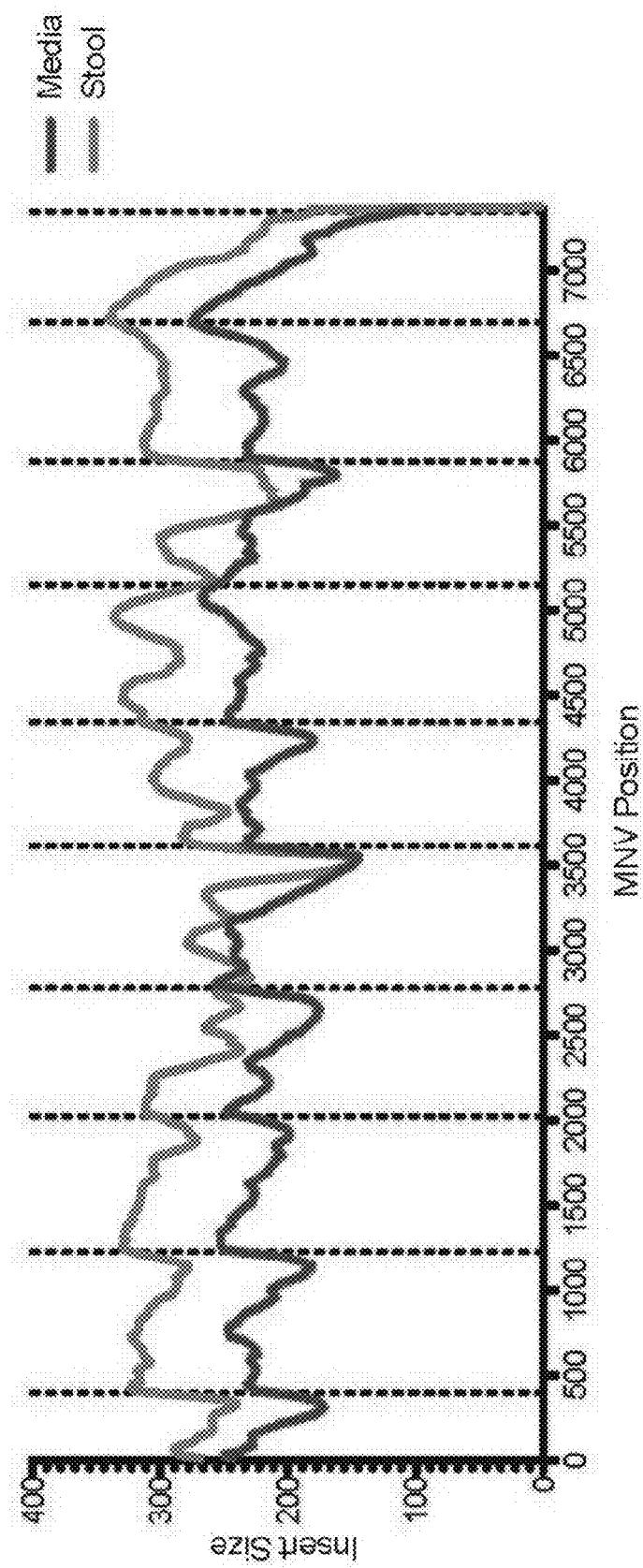

To determine whether the same methodology could be applied to virus-containing samples of animal origin, fecal samples containing MNV-1 were tested. MNV-1 infected mouse fecal material was collected 24 hours post-infection and found to contain $1.1 \times 10^4$ PFU/mL by plaque assay. After homogenization and clarification, 500 uL of fecal material containing $5.5 \times 10^3$ PFU was used to prepare double-stranded cDNA as described above. The library produced from minimal starting material contained 1.6% viral content. Despite the large amount of non-viral sequencing reads, mean reference alignment depth of 2,370 was generated with reads aligning to >99.5% of the genome, as shown in Table 2 above. Similar to culture-derived virus samples and as shown in FIG. 12C, coverage remained high over the entire MNV-1 reference, with increases observable between template-specific priming regions. As shown in FIG. 12D, sequencing library insert size trends were consistent over the entire genome for whole genome MNV-1 libraries. FIG. 12D also illustrates that efficiency of the direct priming technique is observable by altered sequencing library insert sizes nearest the reverse transcription priming sites.

Application to Other Positive-Strand RNA Viruses

To demonstrate the method for other viruses with multiple subtypes, a standard set of universal sequencing primers was designed. Dengue virus (DENV) consists of four genetically related, but distinct serotypes, referred to as DENV-1, -2, -3, and -4. The genome is a positive-strand RNA molecule with a 3' hydroxyl (—OH) group in lieu of a poly-A tail. Four reference genomes representing each serotype were aligned, and six 20-basepair regions with greater than 80% identity were selected across the genome in approximately 1 kb increments. Partially degenerate consensus primer sequences were determined for each region, as shown in Table 1 above. To ensure high coverage at the 5' terminus of the viral genome, a tailed primer was generated that includes a portion of the sequencing adapter inserted by the Nextera XT transposase during sequencing library preparation.

RNA was isolated from the DENV 1-4 laboratory strains grown in C6/36 mosquito cells in culture. Virus titers for these culture supernatants ranged from a low of $5 \times 10^4$ PFU/mL for DENV-3 to $2 \times 10^{10}$ PFU/mL for DENV-2 concentrated through sucrose column centrifugation, as shown in Table 2 above. Double-stranded cDNA synthesis using the universal DENV reverse transcription primer set was performed to prepare Nextera XT libraries of each strain for sequencing, as illustrated by FIGS. 13A-13D. Specifically, FIG. 13, as represented by FIGS. 13A-13D, illustrates serotype agnostic direct primed sequencing of dengue virus according to an example embodiment.

Upon alignment of resulting sequencing reads to respective genomes, libraries were found to contain between

TABLE 2

Viruses Sequenced for Protocol Demonstration and Subsequent Analysis Metrics

| Sample | Source | PFU Isolated | Reads > Q30 | Read Length | Paired End | Aligned % > Q30 | Mean Depth | >1x Coverage | >20x Coverage |
|---|---|---|---|---|---|---|---|---|---|
| MNV-1 | Culture | 3.10E+06 | 2.93E+05 | 300 | Y | 96.41% | 10,154 | 100.00% | 99.89% |
| MNV-1 | Feces | 5.50E+03 | 4.85E+06 | 300 | Y | 1.64% | 2,730 | 99.92% | 99.62% |
| DENV1 | Culture | 8.75E+04 | 1.26E+06 | 150 | Y | 97.23% | 16,201 | 100.00% | 99.95% |
| DENV2 | Culture | 3.92E+08 | 1.78E+06 | 150 | Y | 98.21% | 23,320 | 99.78% | 99.45% |
| DENV3 | Culture | 2.00E+04 | 3.60E+06 | 50 | N | 11.48% | 1,756 | 99.36% | 99.10% |
| DENV4 | Culture | 5.00E+05 | 1.64E+06 | 150 | Y | 72.38% | 15,953 | 99.98% | 99.66% |
| FLU A | Culture | 6.00E+06 | 8.47E+05 | 500 | Y | 60.63% | 10,723 | 100.00% | 99.09% |

Figure 13A:
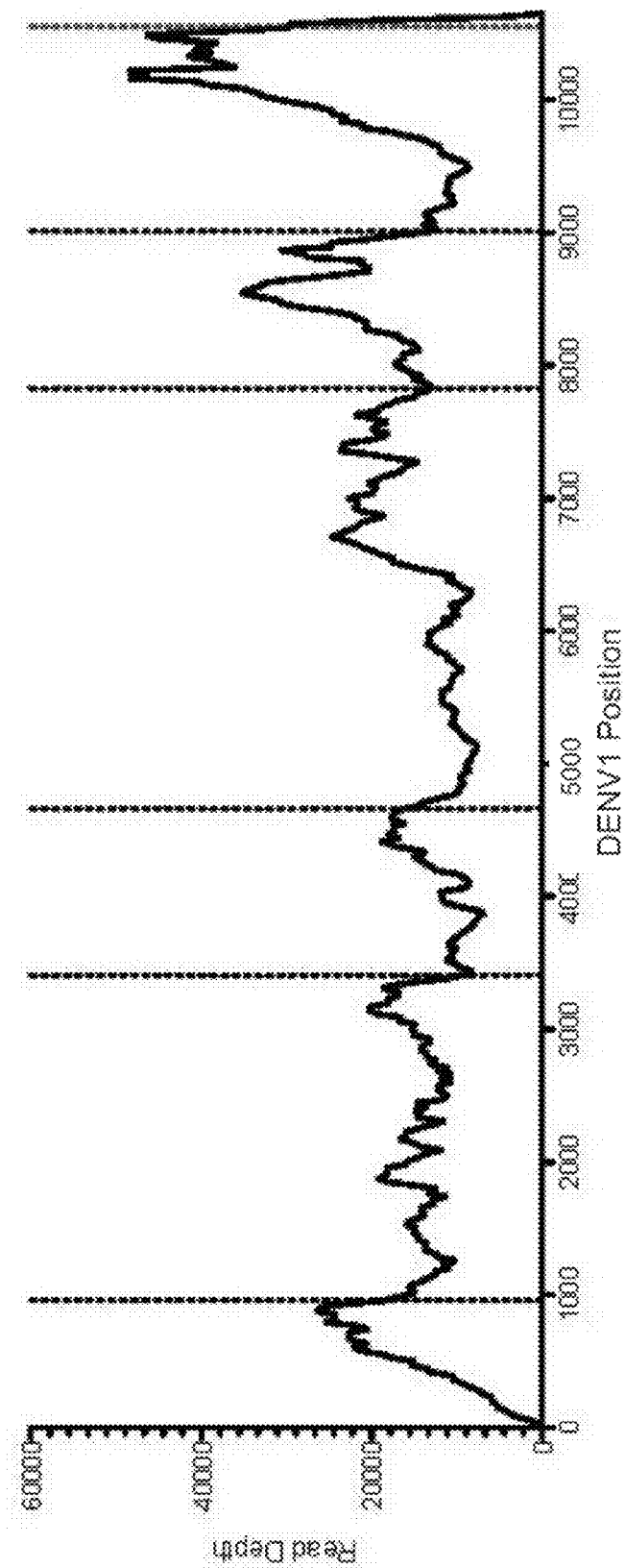
Figure 13B:
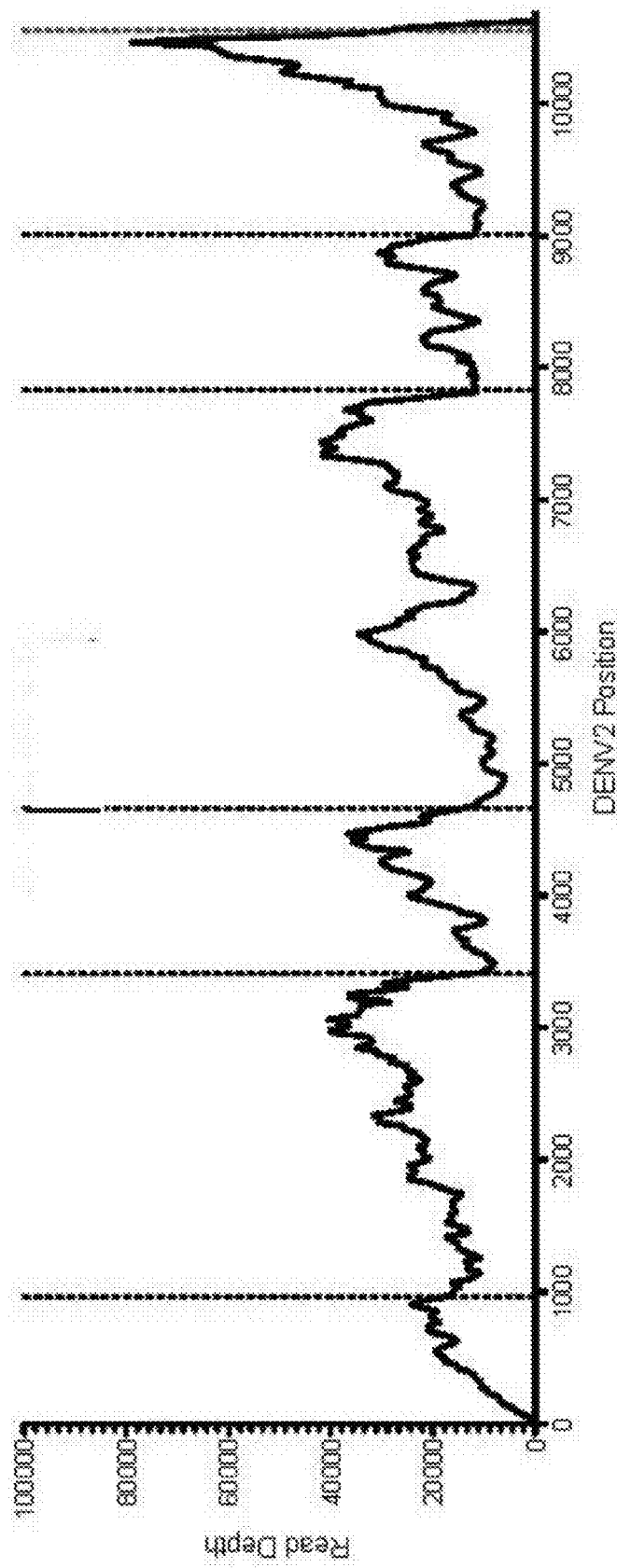
Figure 13C:
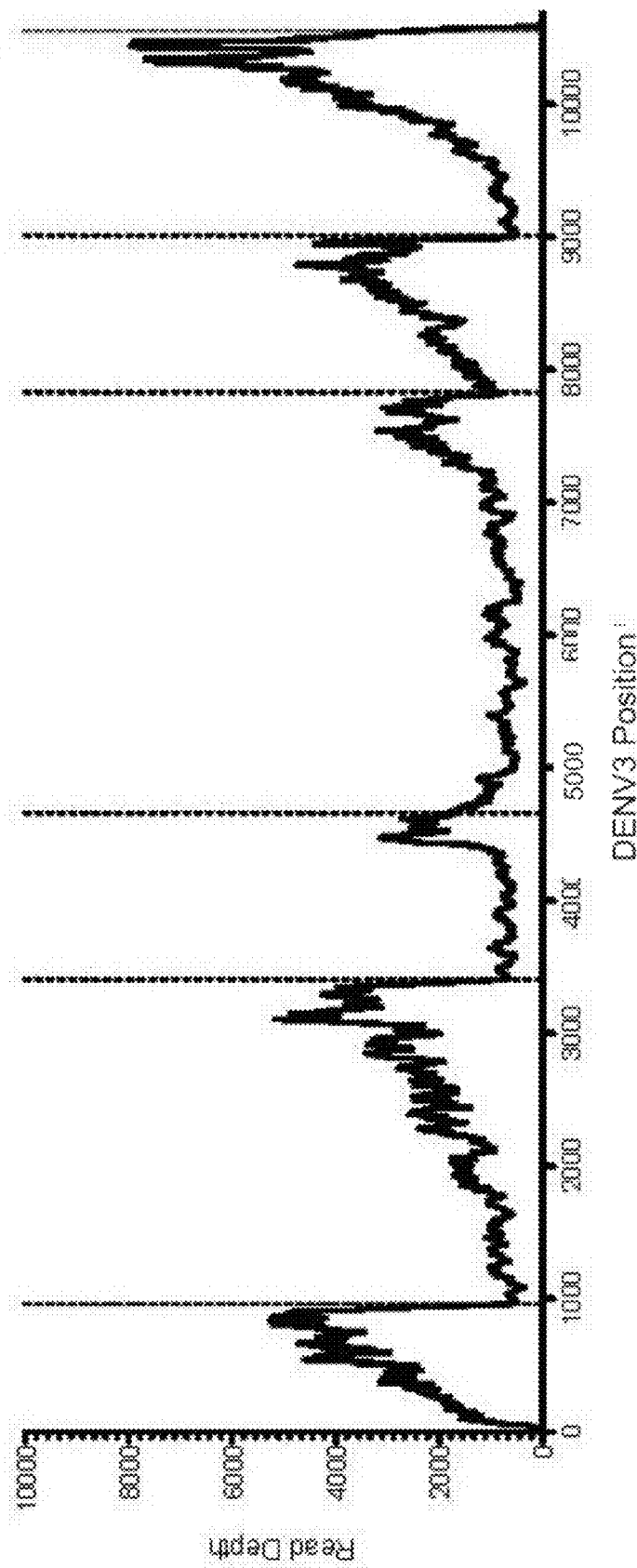
Figure 13D:
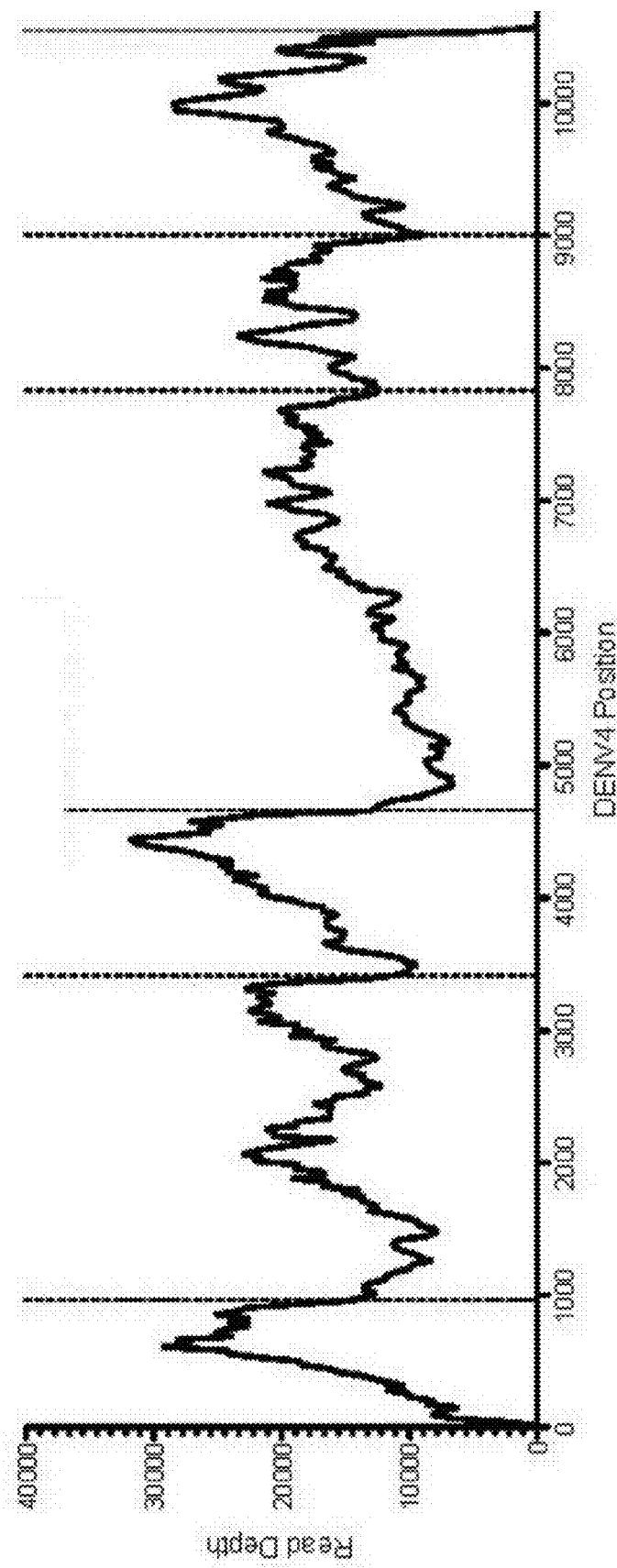
Figure 13E:
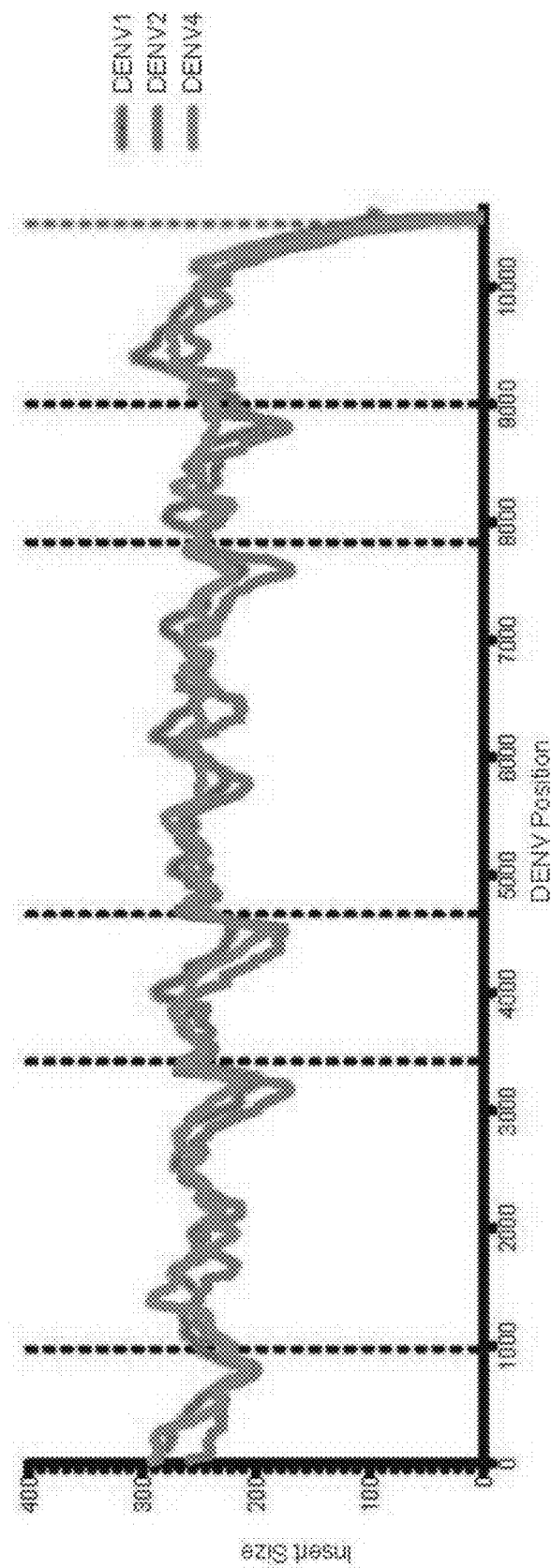

11.9% and 97% viral content, with reads aligning to greater than 99% of each reference genome, as shown in Table 2 above. Variability may be attributed to total viral genome input, number of reads generated, and the type of sequencing performed. Similar to whole genome sequencing of MNV-1, which is also a positive-strand RNA virus, coverage increased at reverse transcription start sites and progressively decreased over the length of the genome until a new priming event was initiated. Additionally, for samples sequenced with paired end reads, insert size was consistent over the entire genome with the exception of the extreme 3' end, indicating successful insertion of the Nextera XT mosaic end during cDNA synthesis by the tailed primer, as shown in FIG. 13E. FIG. 13E also illustrates increased efficiency at the 3' terminus utilizing the tailed reverse transcription primer.

Application to Negative-Sense, Segmented RNA Viruses

Figure 11A:
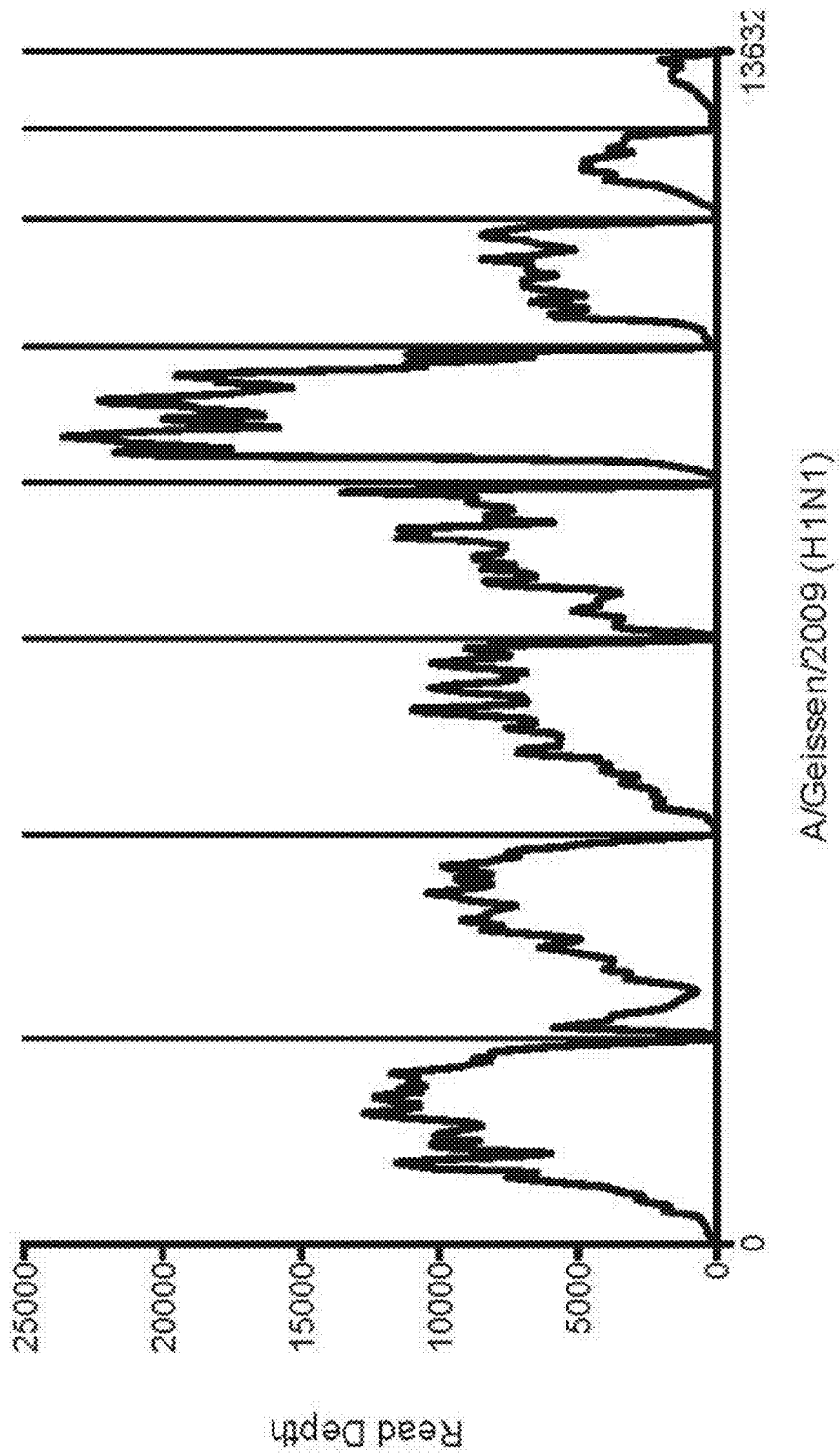
Figure 11B:
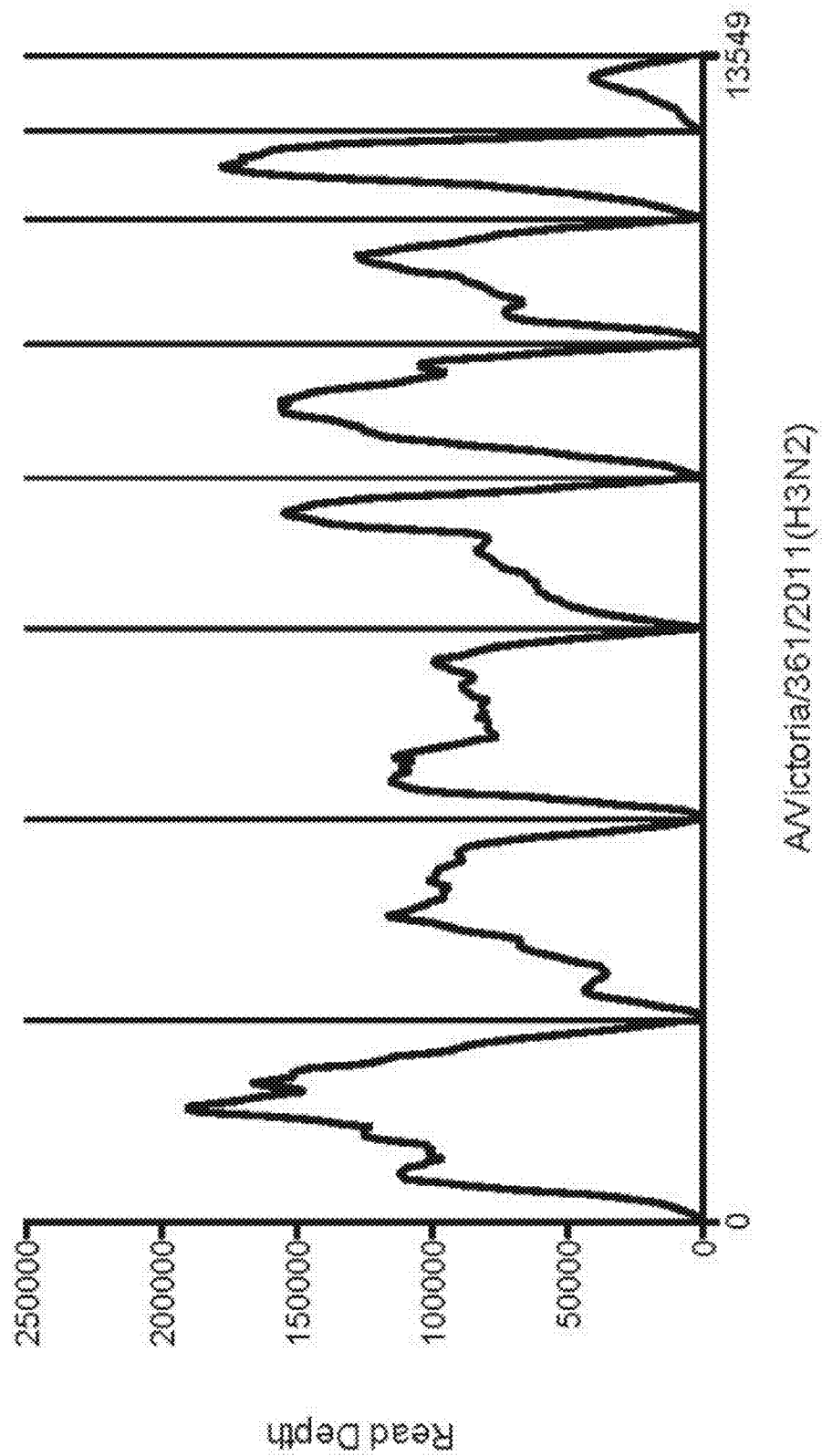
Figure 11C:
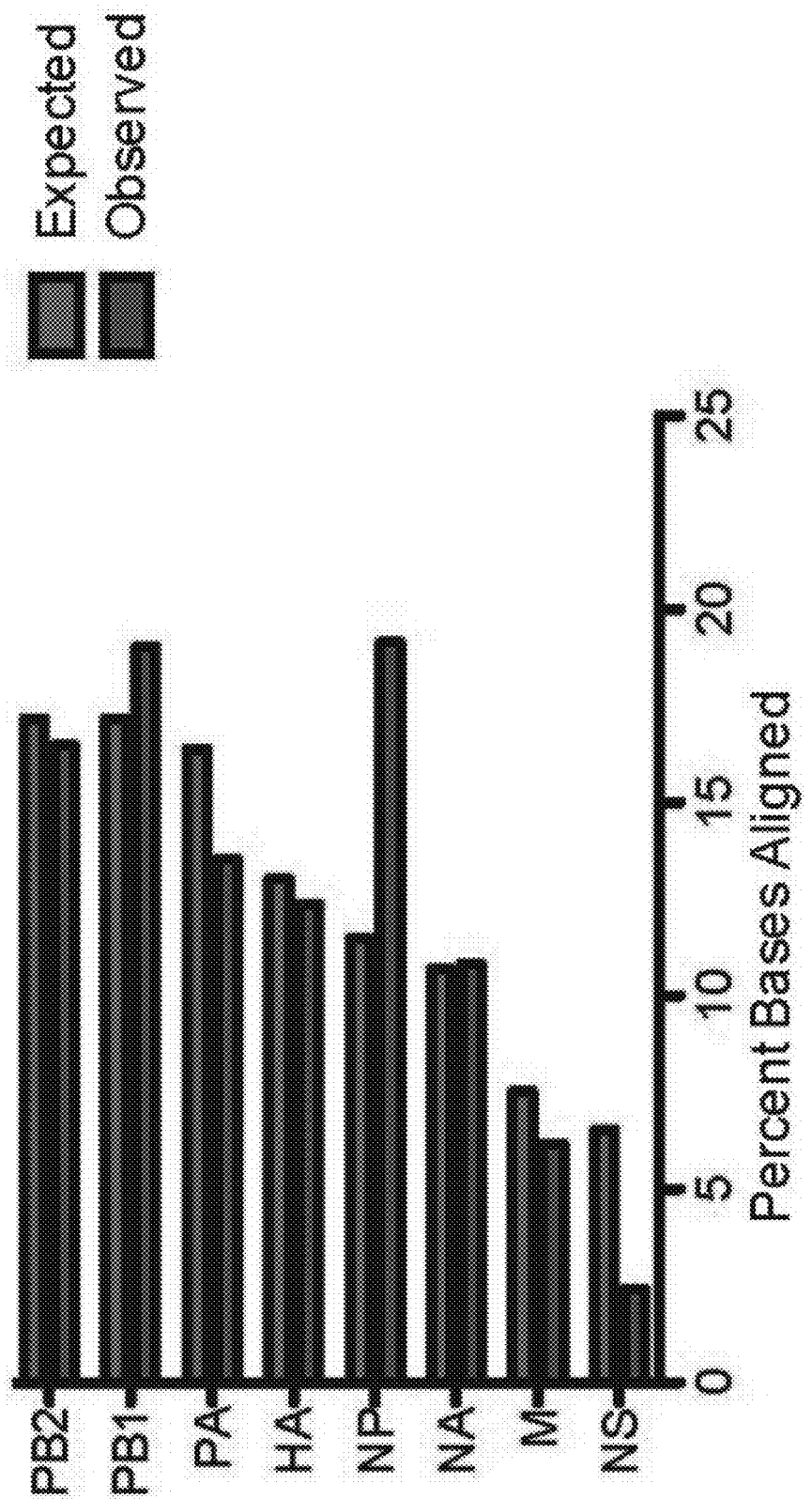

Influenza A is a negative-sense genome consisting of eight independent, unique RNA segments encoding viral proteins. Each RNA molecule contains a 12 base-pair region at the 5' end common to all segments and virus subtypes (i.e. a universal priming region). In order to utilize this priming region for reverse transcription and double-stranded cDNA synthesis, a single tailed primer containing the consensus region from primer MBTuni-13 was combined with the segment inserted by Nextera XT during transposition similar to that used for the DENV universal primer set. To validate this single primer approach, viral RNA from Influenza A/Giessen/6/2009 grown in MDCK tissue culture cells was isolated followed by double-stranded cDNA synthesis, Nextera XT library preparation, and sequencing. The resulting library contained 60.63% viral content, as shown in Table 2 above with consistently high depth across each genome segment, as illustrated by FIG. 11A. FIG. 11A specifically illustrates high coverage on a 2009 H1N1 virus by a universal Influenza A reverse transcription primer modified to include the Nextera XT mosaic end insertion site. Insert size was reduced nearest the tailed priming event but consistent over the remainder of each genome segment, as shown in FIG. 11B. Bases mapped per segment were within 0.2 fold of the expected value based on genome segment size, with the exception of a 1.67 fold increase for the NP RNA segment and a reduction of 0.63 fold for the NS segment, as shown in FIG. 11C, which illustrates the comparison of the percentage of bases aligning to each genome segment with the observed alignment rate.

Figure 11D:
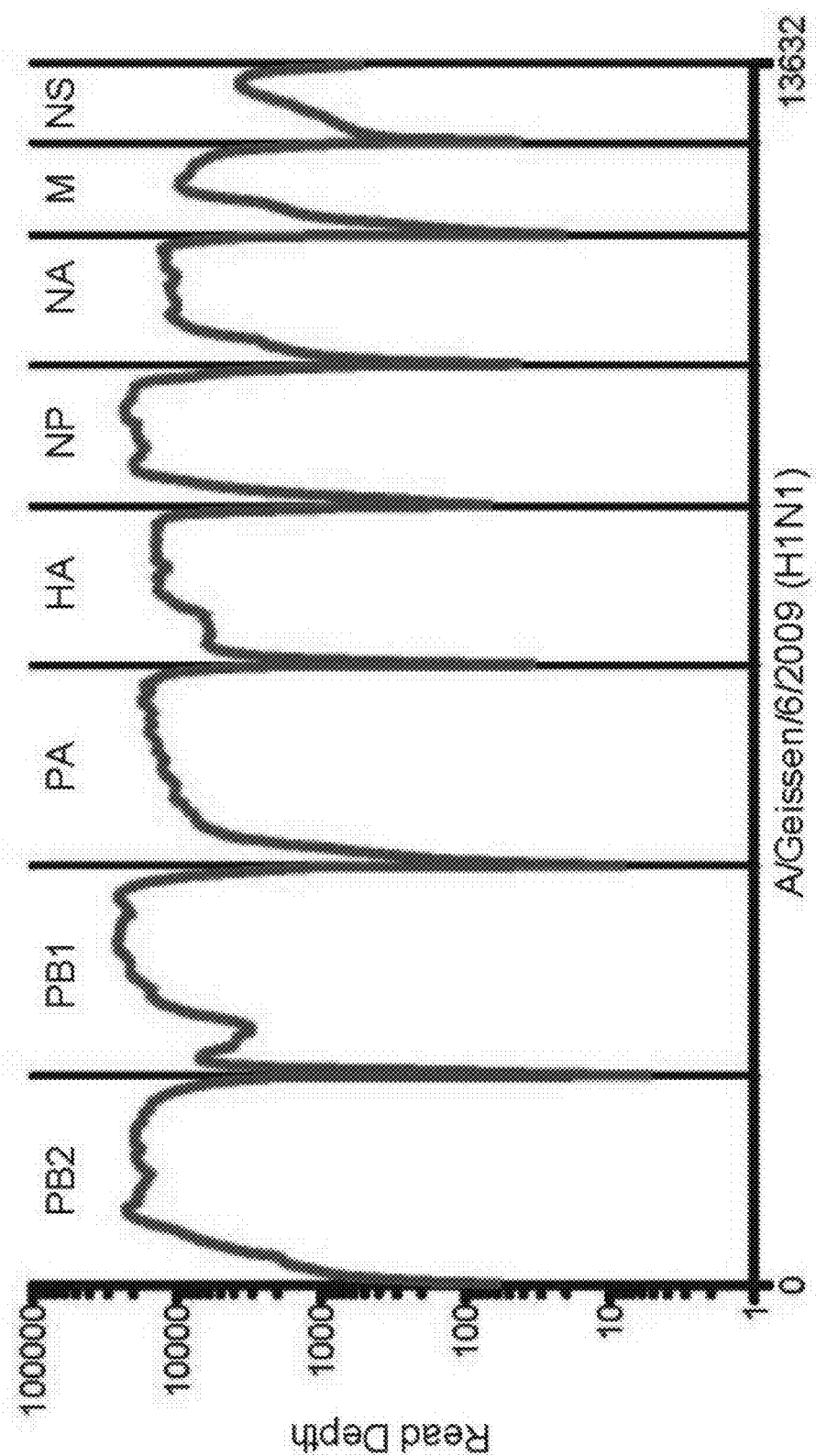

Importantly, samples sequenced at such high depth display several hundred-fold coverage over the entire 5' end of each genome segment, including regions past the mosaic end tailed primer. Greater than 99% of the reference was represented with the lowest coverage at the extreme 3' termini of each genome segment, as shown in FIG. 11D, which illustrates read alignment based on depth of coverage with a log-scale y-axis. This trend was also observed in MNV-1 and DENV samples and is likely a result of the second strand fill in process.

Rapid Strain and Serotype Identification by k-Mer Based Read Matching

Processing quality-filtered reads through both a full Kraken database, containing all bacteria and viruses, and the virus-only Kraken implementation resulted in accurate assignment of species for each virus sequenced at a rate comparable to reference alignment, as shown in Table 3.

TABLE 3

Comparison of Reference Alignment and k-mer Based Read Matching for Speciation

| Sample | Paired End | Read Length | Reads > Q30 | Bowtie 2 Aligned | Full Kraken ID | ID/ Align | Virus Kraken ID | ID/ Align | Flu A Kraken ID | ID/ Align |
|---|---|---|---|---|---|---|---|---|---|---|
| MNV-1 | Y | 300 | 2.93E+05 | 2.83E+05 | 2.92E+05 | 103% | 2.92E+05 | 103% | — | — |
| MNV-1 | Y | 300 | 4.85E+06 | 7.98E+04 | 7.20E+04 | 90% | 7.21E+04 | 90% | — | — |
| DENV1 | Y | 150 | 1.26E+06 | 1.22E+06 | 9.75E+05 | 80% | 9.75E+05 | 80% | — | — |
| DENV2 | Y | 150 | 1.78E+06 | 1.59E+06 | 1.65E+06 | 104% | 1.65E+06 | 104% | — | — |
| DENV3 | N | 50 | 3.60E+06 | 4.14E+06 | 1.41E+05 | 34% | 1.41E+05 | 34% | — | — |
| DENV4 | Y | 150 | 1.64E+06 | 1.19E+06 | 9.59E+05 | 81% | 9.59E+05 | 81% | — | — |
| FLU A | Y | 500 | 8.47E+05 | 5.14E+05 | 2.15E+05 | 42% | 2.15E+05 | 42% | 4.94E+05 | 96% |

Importantly, the modified virus implementation was almost identical in performance to the full database, allowing for a much smaller computational footprint. While Influenza A was properly identified using the pan-virus database, the overall read identification rate was low in comparison to reference alignment, and speciation was frequently misassigned. These errors were due to the fact that Refseq contains only 40 Influenza A segments representing a total of five subtypes, making this database insufficient for high resolution identification. To overcome this deficiency, we constructed an Influenza A specific database using all complete segments acquired from the Influenza research database (fludb.org). In total, this database contains 226,482 sequences representing 125 subtypes, organized in taxonomy according to genome segment, subtype, year, and strain. The resulting output of this analysis is the identification of a lowest common ancestor for each genome segment, which can then be used to educate reference alignment and reference-based assembly.

Exemplary Embodiments

Having described various aspects and embodiments of the invention herein, further specific embodiments of the invention include those set forth in the following paragraphs.

In some example embodiments, a method for limited input whole genome sequencing of RNA viruses is provided. In general, the method for limited input whole genome sequencing of RNA viruses, according to certain embodiments, comprises isolating a viral RNA sample, converting the viral RNA sample to a double-stranded viral cDNA sample, constructing a double-stranded viral cDNA amplicon library from the double-stranded viral cDNA sample, and sequencing the double-stranded viral cDNA amplicon library to obtain a double-stranded viral cDNA sample sequencing read. In some embodiments, the method further comprises analyzing the double-stranded viral cDNA sample sequencing read with an ultrafast read classifier. According to certain embodiments, the method comprises a completion time of from about 5 to about 15 hours and a hands-on time of from about 0.5 hours to about 5 hours.

In accordance with an example embodiment, isolating the viral RNA sample comprises extracting RNA from a supernatant to form an RNA extract sample and depleting DNA from the RNA extract sample. In some embodiments, extracting RNA from the supernatant comprises magnetic bead-based nucleic acid isolation. In certain embodiments, the supernatant comprises about $10^3$ RNA viruses. In some embodiments, the supernatant comprises an in vitro supernatant or an in vivo supernatant. According to an example embodiment, converting the viral RNA sample to the double-stranded viral cDNA sample comprises priming first strand cDNA synthesis using an oligonucleotide targeting a highly conserved region of a viral genome, synthesizing a second cDNA strand with RNase H, DNA ligase, and DNA polymerase I to form the double-stranded viral cDNA sample, and purifying the double-stranded viral cDNA sample.

In accordance with an example embodiment, constructing the double-stranded viral cDNA amplicon library comprises performing tagmentation reactions on the double-stranded viral cDNA sample to obtain the double-stranded viral cDNA amplicon library, purifying the double-stranded viral cDNA amplicon library, quantifying the double-stranded viral cDNA amplicon library, and pooling multiplexed double-stranded viral cDNA amplicon libraries. In some embodiments, one set of primers is effective in performing tagmentation reactions across different strains within a viral family.

In accordance with an example embodiment, sequencing the double-stranded viral cDNA amplicon library comprises denaturing the double-stranded viral cDNA amplicon library, loading the double-stranded viral cDNA amplicon library onto a sequencer, and running the sequencer to produce a double-stranded viral cDNA sample sequencing read. In some embodiments, sequencing the double-stranded viral cDNA amplicon library comprises sequencing from about 0.1 pg to about 10 pg converted viral genomes. According to certain embodiments, the RNA viruses comprise segmented genomes or non-segmented genomes. In some embodiments, the RNA viruses comprise at least one of double-stranded RNA viruses, positive-sense single-stranded RNA viruses, negative-sense single-stranded RNA viruses, or any combination thereof.

In another aspect, a method of analyzing RNA virus samples via an ultrafast read classifier is provided. In general, the method of analyzing RNA virus samples via an ultrafast read classifier, according to certain embodiments, comprises querying each double-stranded viral cDNA sequencing read for sequence alignment with existing reference genomes in at least one database and identifying each double-stranded viral cDNA sequencing read as belong to an RNA viral species. In some embodiments, the method further comprises identifying lowest common ancestors of high similarity matches between each double-stranded viral cDNA sequencing read and existing reference genomes. According to certain embodiments, the method has a sequence alignment with existing reference genomes from about 90% to about 100%. In some embodiments, the at least one database comprises at least one of a full metagenomics implementation, a pan-virus implementation, a virus-specific implementation, or any combination thereof. In certain embodiments, the ultrafast read classifier analyzes from about 3 million to about 4 million double-stranded viral cDNA sequencing reads in from about 1 minute to about 5 minutes. In some embodiments, the ultrafast read classifier identifies nearest neighbor RNA viruses in from about 1 minute to about 15 minutes.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A method for limited input whole genome sequencing of orthomyxoviruses, noroviruses, flaviviruses, or ebola viruses, the method comprising:
    isolating a orthomyxovirus, norovirus, flavivirus, or ebola virus viral RNA sample;
    converting the viral RNA sample to a double-stranded viral cDNA sample, wherein the converting includes:
        priming first strand cDNA synthesis using an oligonucleotide primer specific for a highly conserved region of a viral genome, wherein the highly conserved region is common to all subtypes of the viral genome as a means of replication,
        synthesizing a second cDNA strand with RNase H, DNA ligase, and DNA polymerase I to form the double-stranded viral cDNA sample, and
        purifying the double-stranded viral cDNA sample;
    constructing a double-stranded viral cDNA amplicon library from the double-stranded viral cDNA sample; and
    sequencing the double-stranded viral cDNA amplicon library to obtain a double-stranded viral cDNA sample sequencing read.

2. The method according to claim 1, wherein isolating the viral RNA sample comprises:
    extracting RNA from a supernatant to form an RNA extract sample; and
    depleting DNA from the RNA extract sample.

3. The method according to claim 2, wherein extracting RNA from the supernatant comprises magnetic bead-based nucleic acid isolation.

4. The method according to claim 2, wherein the supernatant comprises about $10^5$ RNA viruses.

5. The method according to claim 2, wherein the supernatant comprises an in vivo supernatant.

6. The method according to claim 1, wherein constructing the double-stranded viral cDNA amplicon library comprises:
    performing tagmentation reactions on the double-stranded viral cDNA sample to obtain the double-stranded viral cDNA amplicon library;
    purifying the double-stranded viral cDNA amplicon library;
    quantifying the double-stranded viral cDNA amplicon library; and
    pooling multiplexed double-stranded viral cDNA amplicon libraries.

7. The method according to claim 6, wherein one set of primers is effective in performing tagmentation reactions across different strains within a viral family.

8. The method according to claim 1, wherein sequencing the double-stranded viral cDNA amplicon library comprises:
    denaturing the double-stranded viral cDNA amplicon library;

loading the double-stranded viral cDNA amplicon library onto a sequencer; and running the sequencer to obtain the double-stranded viral cDNA sample sequencing read.

9. The method according to claim 1, wherein sequencing the double-stranded viral cDNA amplicon library comprises sequencing from about 0.1 pg to about 10 pg converted viral genomes.

10. The method according to claim 1, further comprising analyzing the double-stranded viral cDNA sample sequencing read with an ultrafast read classifier.

11. The method according to claim 10, wherein analyzing the double-stranded viral cDNA sample sequencing read with an ultrafast read classifier further comprises:

querying at least one database; and identifying the double-stranded viral cDNA sample sequencing read as belonging to an RNA viral species.

12. The method according to claim 11, wherein the at least one database comprises at least one of a full metagenomics implementation, a pan-virus implementation, a virus-specific implementation, or any combination thereof.

13. The method according to claim 10, wherein the ultrafast read classifier analyzes from about 3 million reads to about 4 million double-stranded viral cDNA sample sequencing reads in from about 1 minute to about 5 minutes and the ultrafast read classifier has a sequence alignment with existing reference genomes of from about 90% to about 100%.

14. The method according to claim 10, wherein the ultrafast read classifier identifies nearest neighbor RNA viruses in from about 1 minute to about 15 minutes.

15. The method according to claim 1, wherein the RNA viruses comprise non-segmented genomes.

16. The method according to claim 1, wherein the RNA viruses comprise negative-sense single-stranded RNA viruses.

17. The method according to claim 1, wherein the method comprises a completion time of from about 5 hours to about 15 hours and a hands-on time of from about 0.5 hours to about 5 hours.

18. The method according to claim 1, wherein the supernatant comprises an in vitro supernatant.

19. The method according to claim 1, wherein the RNA viruses comprise segmented genomes.

20. The method according to claim 1, wherein the RNA viruses comprise double-stranded RNA viruses.

* * * * *